(12) United States Patent
Haghighi-Mood et al.

(10) Patent No.: US 11,937,874 B2
(45) Date of Patent: Mar. 26, 2024

(54) MULTI-MODAL CATHETER FOR IMPROVED ELECTRICAL MAPPING AND ABLATION

(71) Applicant: Sirona Medical Technologies, Inc., Andover, MA (US)

(72) Inventors: Ali Haghighi-Mood, Andover, MA (US); Richard Jonathan Cohen, Newton, MA (US)

(73) Assignee: Sirona Medical Technologies, Inc., Andover, MA (US)

( * ) Notice: Subject to any disclaimer, the term of this patent is extended or adjusted under 35 U.S.C. 154(b) by 0 days.

(21) Appl. No.: 17/817,215

(22) Filed: Aug. 3, 2022

(65) Prior Publication Data

US 2022/0370124 A1 Nov. 24, 2022

Related U.S. Application Data

(63) Continuation of application No. 17/559,273, filed on Dec. 22, 2021, which is a continuation of application
(Continued)

(51) Int. Cl.
*A61B 18/14* (2006.01)
*A61B 18/00* (2006.01)

(52) U.S. Cl.
CPC ............ *A61B 18/1492* (2013.01); *A61B 2018/00267* (2013.01); *A61B 2018/00375* (2013.01);
(Continued)

(58) Field of Classification Search
CPC ...... A61B 18/1492; A61B 2018/00267; A61B 2018/00375; A61B 2018/00577;
(Continued)

(56) References Cited

U.S. PATENT DOCUMENTS 5,293,869 A 3/1994 Edwards et al.
6,572,612 B2 * 6/2003 Stewart ............. A61B 18/1492
606/41
(Continued)

FOREIGN PATENT DOCUMENTS

WO 2019143960 A1 7/2019

OTHER PUBLICATIONS

International Search Report and Written Opinion for International Patent Application No. PCT/US2020/058847, dated Apr. 26, 2021, 12 pages.

*Primary Examiner* — Michael F Peffley
*Assistant Examiner* — Amanda L Zink
(74) *Attorney, Agent, or Firm* — Mintz, Levin, Cohn, Ferris, Glovsky & Popeo, PC

(57) ABSTRACT

Various catheters are provided herein for recording, mapping, and/or ablating target tissue to reduce or eliminate unwanted electrical impulses. In one embodiment, a catheter can have a handle, an elongate body, and an end effector. The end effector has expanded and contracted configurations and can rotate about the elongate body. A plurality of electrodes can also be disposed on the end effector for recording, mapping, and/or ablating target tissue surrounding the catheter. The handle can guide the end effector through transitioning between the configurations and rotating about the elongate body.

30 Claims, 21 Drawing Sheets

Related U.S. Application Data

No. 17/089,354, filed on Nov. 4, 2020, now Pat. No. 11,291,500.

(60) Provisional application No. 62/931,066, filed on Nov. 5, 2019.

(52) U.S. Cl.
CPC ............... *A61B 2018/00577* (2013.01); *A61B 2018/1467* (2013.01); *A61B 2218/002* (2013.01)

(58) Field of Classification Search
CPC .. A61B 2018/00839; A61B 2018/1467; A61B 2218/002
See application file for complete search history.

(56) References Cited

U.S. PATENT DOCUMENTS

| | | | |
|---|---|---|---|
| 9,717,558 B2 | 8/2017 | Desai | |
| 10,130,423 B1* | 11/2018 | Viswanathan | A61B 18/1492 |
| 10,485,611 B2 | 11/2019 | Haghighi-mood et al. | |
| 11,291,500 B2 | 4/2022 | Haghighi-mood et al. | |
| 2004/0153025 A1 | 8/2004 | Seifert et al. | |
| 2005/0119668 A1* | 6/2005 | Teague | A61B 17/221 606/127 |
| 2005/0283140 A1 | 12/2005 | Jensen et al. | |
| 2005/0288730 A1* | 12/2005 | Deem | A61N 1/36017 607/42 |
| 2007/0100254 A1 | 5/2007 | Murakami et al. | |
| 2010/0204560 A1* | 8/2010 | Salahieh | A61B 5/01 606/41 |
| 2013/0172715 A1* | 7/2013 | Just | A61B 5/6858 606/41 |
| 2014/0276613 A1* | 9/2014 | Goodman | A61B 18/1492 604/95.04 |
| 2015/0238251 A1 | 8/2015 | Shikhman et al. | |
| 2016/0144091 A1* | 5/2016 | Breedon | A61M 60/497 264/129 |
| 2016/0166270 A1* | 6/2016 | Hera | A61B 17/221 606/127 |
| 2016/0192981 A1 | 7/2016 | Dimmer et al. | |
| 2017/0224375 A1 | 8/2017 | Robertson et al. | |
| 2018/0193590 A1 | 7/2018 | Rajagopalan et al. | |
| 2018/0199993 A1 | 7/2018 | Mayse et al. | |
| 2018/0333202 A1 | 11/2018 | Hancock et al. | |
| 2019/0105074 A1 | 4/2019 | Kónya | |
| 2019/0239811 A1 | 8/2019 | Just et al. | |
| 2021/0128233 A1 | 5/2021 | Haghighi-mood et al. | |
| 2022/0110677 A1 | 4/2022 | Haghighi-mood et al. | |
| 2022/0192722 A1* | 6/2022 | Harshman | A61B 17/8819 |

\* cited by examiner

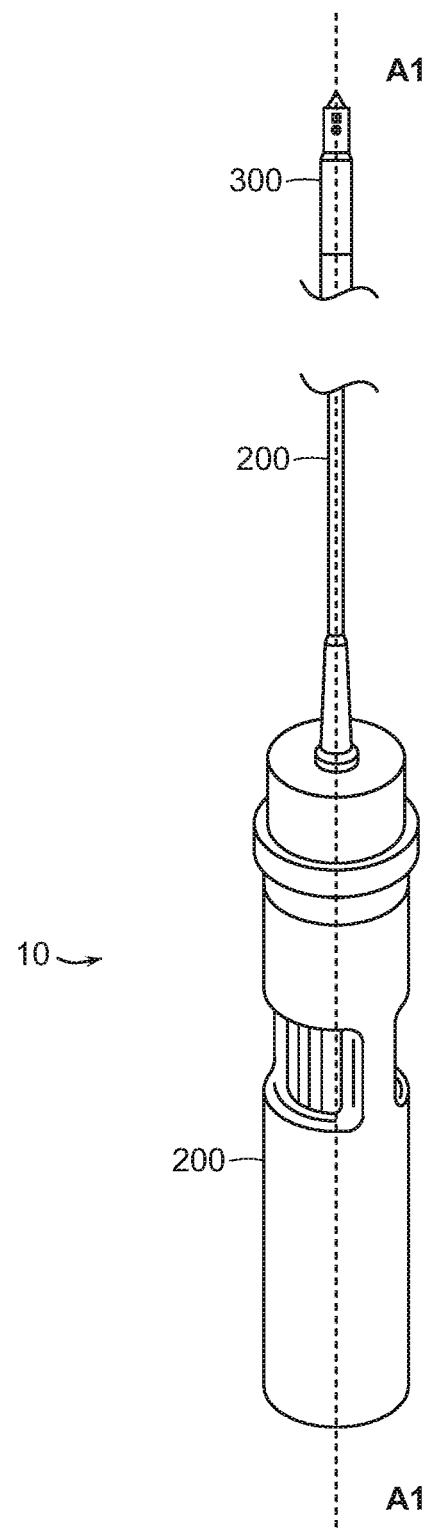

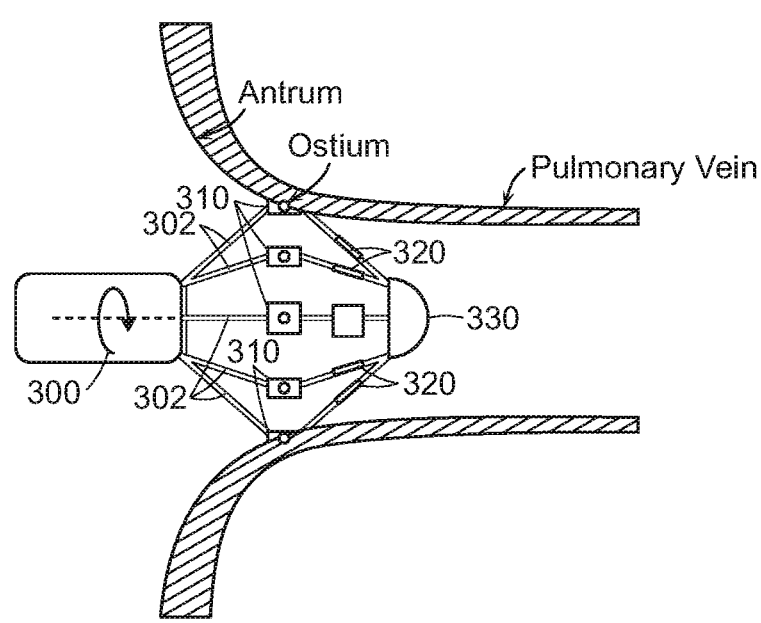
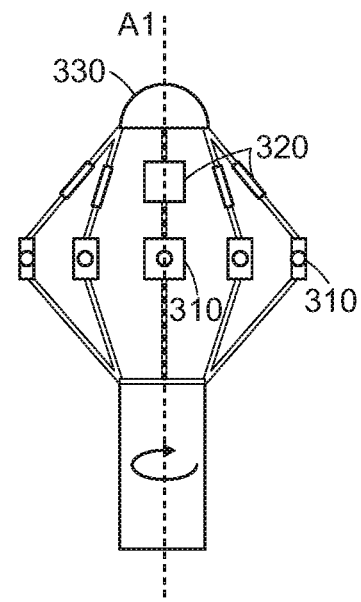
FIG. 7A
FIG. 7B
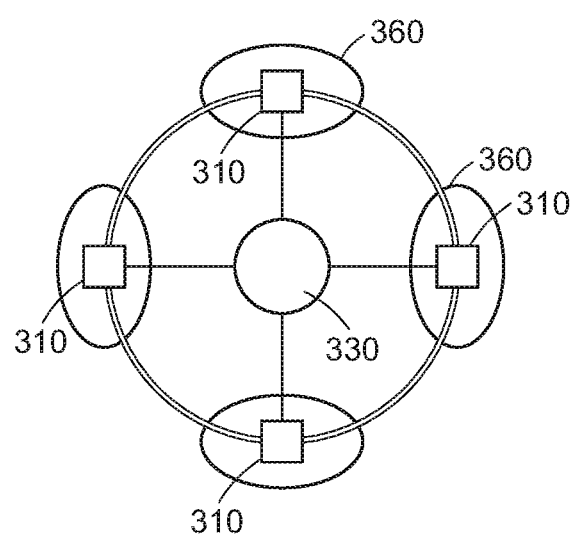
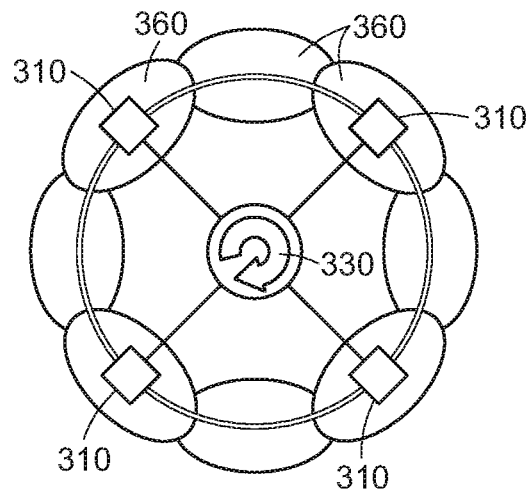
FIG. 7C
FIG. 7D

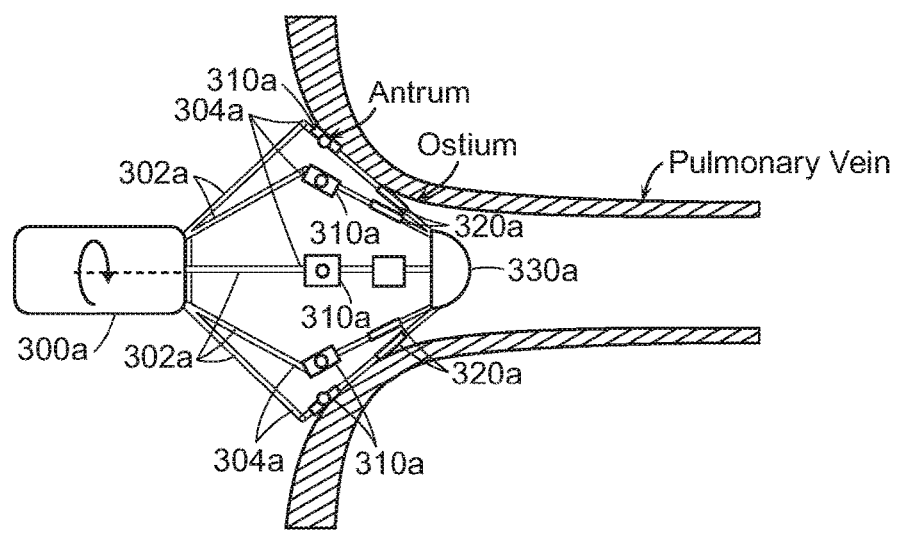
FIG. 7E
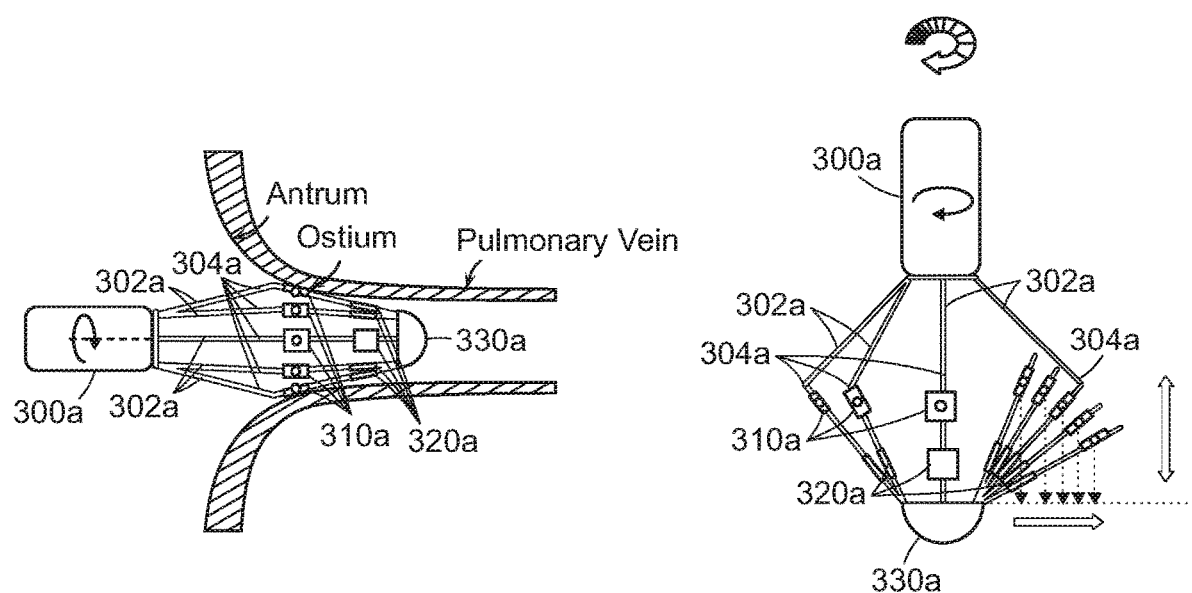
FIG. 7F
FIG. 7G

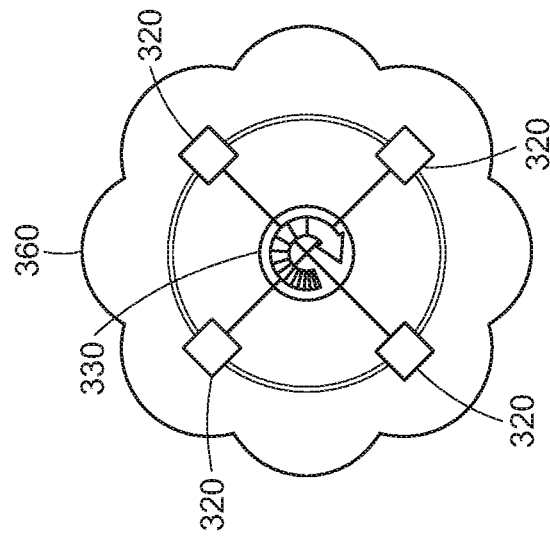
FIG. 10B1
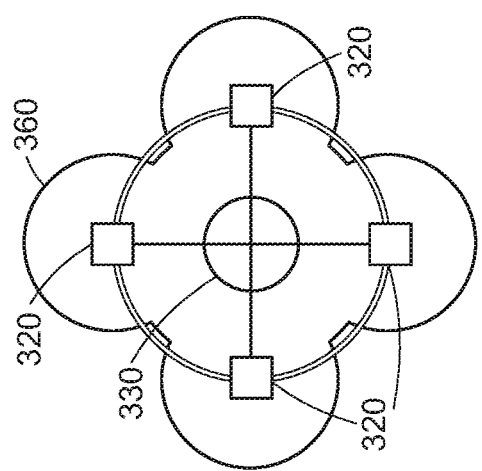
FIG. 10B
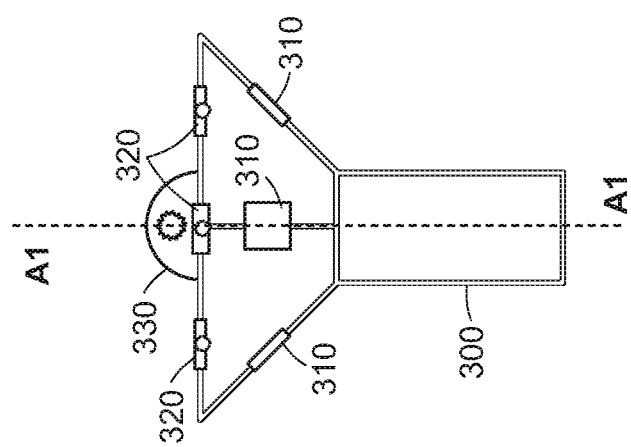
FIG. 10A

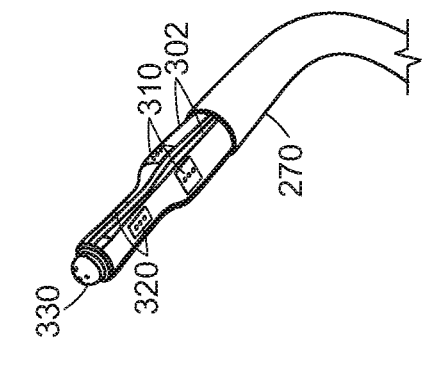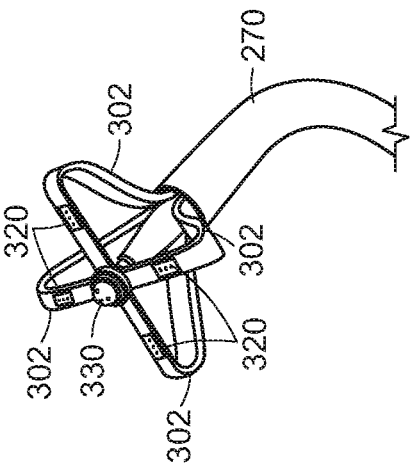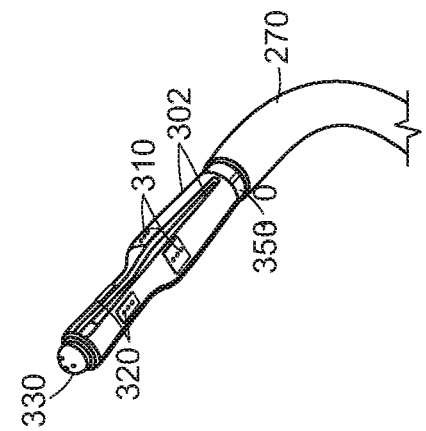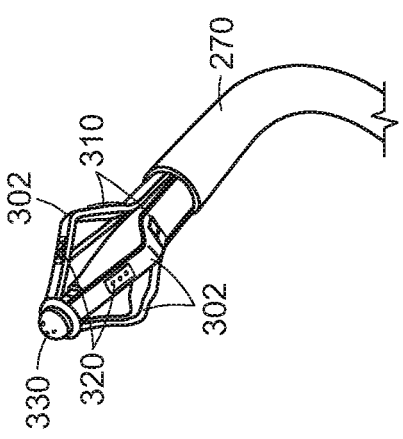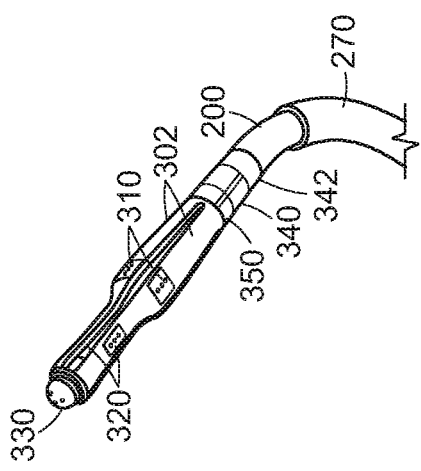

FIG. 11
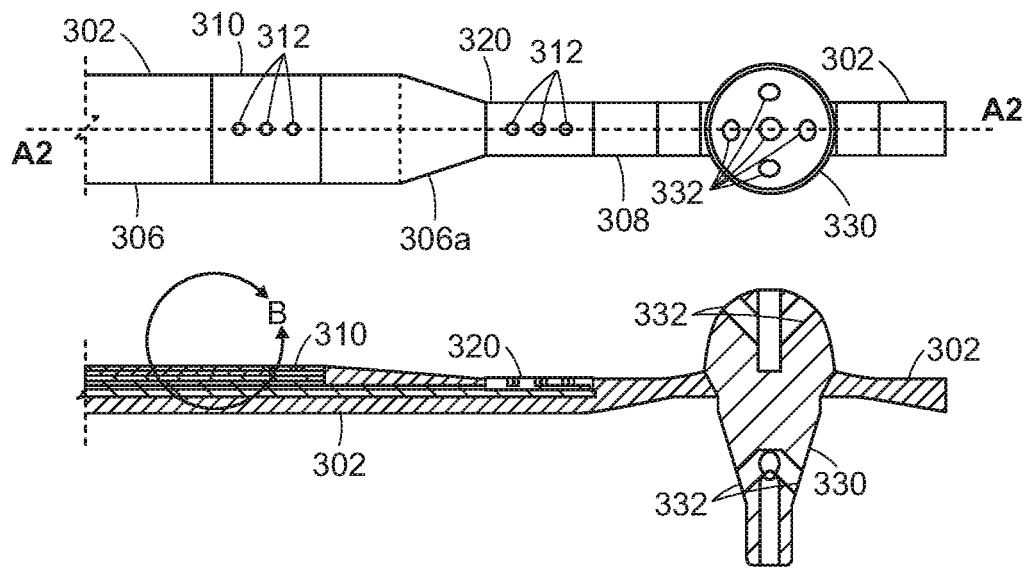
FIG. 12
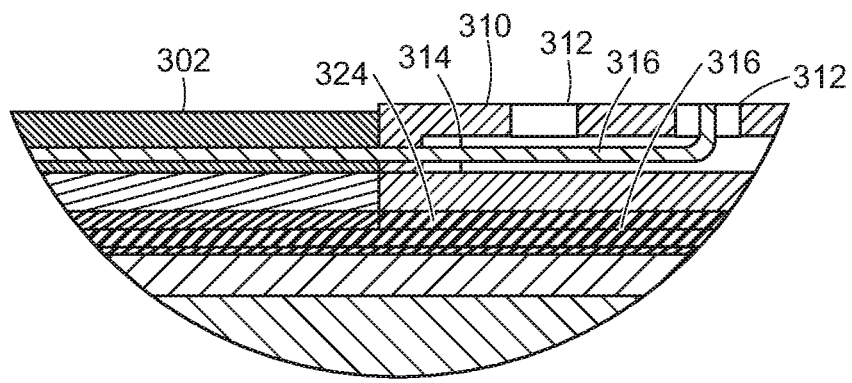
FIG. 13

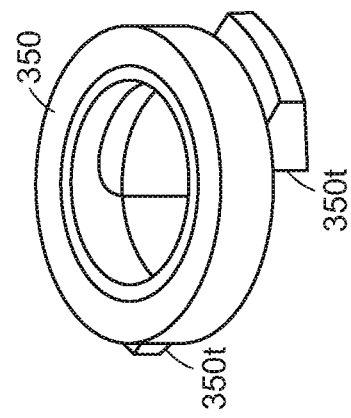
FIG. 16B
FIG. 18
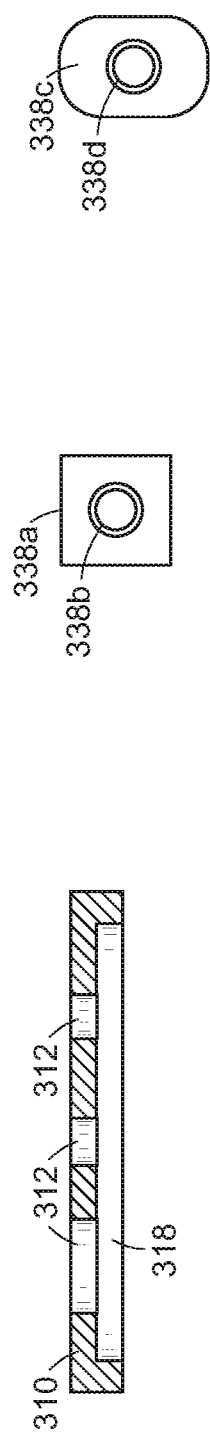
FIG. 16A
FIG. 16
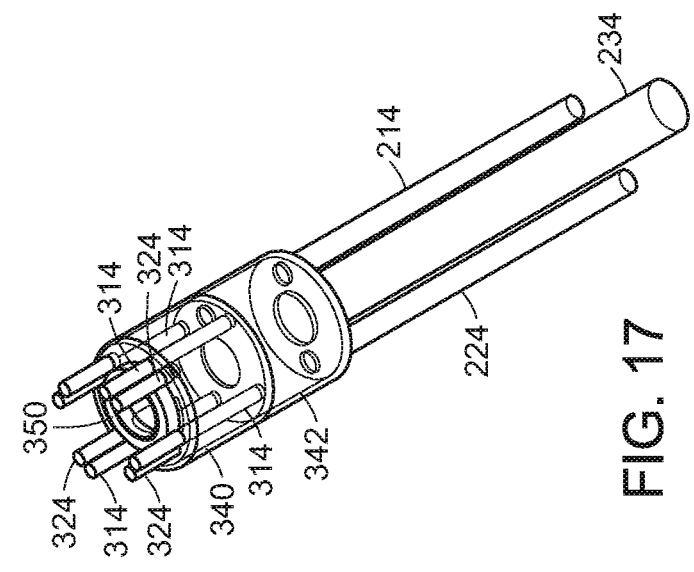
FIG. 17

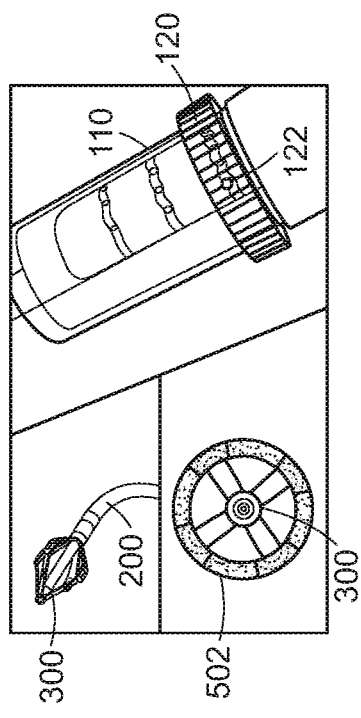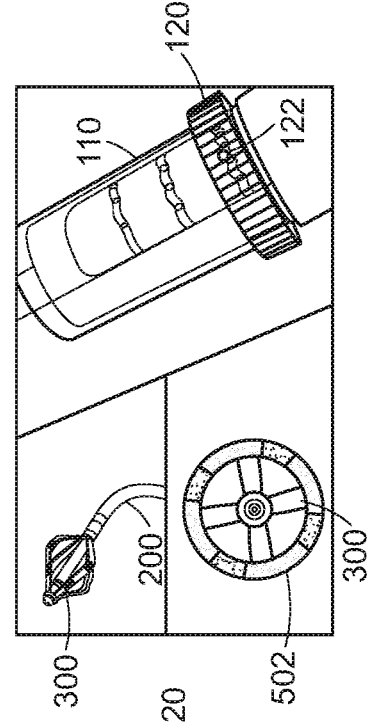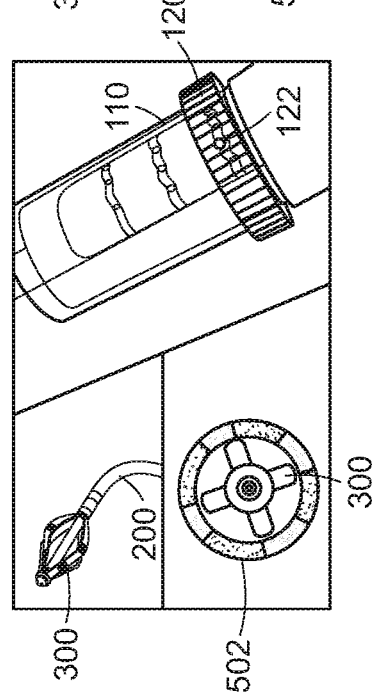

MULTI-MODAL CATHETER FOR IMPROVED ELECTRICAL MAPPING AND ABLATION

CROSS-REFERENCE TO RELATED APPLICATIONS

This application is a continuation of U.S. application Ser. No. 17/559,273, filed on Dec. 22, 2021, and entitled "Multi-Modal Catheter For Improved Electrical Mapping and Ablation," which is a continuation of U.S. application Ser. No. 17/089,354, filed on Nov. 4, 2020 (now U.S. Pat. No. 11,291,500), and entitled "Multi-Modal Catheter For Improved Electrical Mapping and Ablation," which claims the benefit of priority to U.S. Provisional App. No. 62/931,066 of Haghighi-Mood et al., filed on Nov. 5, 2020 and entitled "Multi-Modal Catheter for Improved Electrical Mapping and Ablation," which are incorporated herein by reference in their entireties.

FIELD

Catheters, and in particular recording, mapping, and irrigated ablation catheters, are provided, as well as methods for using the same.

BACKGROUND

Mechanical contraction of cardiac muscle is controlled by the propagation of various electrical impulses to control operation of the heart and pumping of blood through a body. Various specialized cells in the heart control proper functioning and rhythm of beats. For example, some cardiac muscle cells in the sino-atrial node can automatically initiate an electrical impulse on a regular basis to serve as the heart's normal pacemaker, and other cardiac muscle cells in the atrio-ventricular-node can serve to delay conduction of the electrical impulse between the heart's atria and the heart's ventricles. Other cells can rapidly distribute electrical impulses to different regions of the heart to allow contraction in a synchronous fashion and enhance the heart's function.

However, a variety of disorders can negatively affect the heart, such as disorders negatively affecting the electrical functioning of the heart like arrhythmias that cause too slow a heart rate (bradyarrhythmias) or too rapid a heart rate (tachyarrhythmias). These various disorders can be caused through a variety of mechanisms, such as disorders of impulse formation causing abnormal automaticity of the heart's normal pacemaker function and disorders of impulse conduction caused by partial or complete block of electrical impulses.

There are various treatments for heart rhythm disturbances, such as through use of drugs, insertion of a pacemaker, and/or tissue ablation. However, there are many problems and limitations of the currently available methods and devices used for treatment. Drugs require ongoing, often daily administration and commonly cause unwanted side effects, insertion of a pacemaker is invasive and is generally unsuccessful in treating tachyarrhythmias, and current tissue ablation techniques and tools can be complicated, time-consuming, and may have limited success in treatment of cardiac arrhythmias. For example, because of the complexities of recording and mapping electrical impulses in cardiac tissue, ablation procedures can be long, expensive, and can require highly trained medical professionals. Furthermore, even after target site(s) are identified, successful ablation of the target site(s) is difficult to achieve. Even an ablation procedure that appears to successfully abolish arrhythmia while the procedure is ongoing may eventually prove to be a failure because the arrhythmia can recur at a later time. Recurrence may be due in part from a failure to successfully identify the target site(s) for ablation and/or failure to successfully ablate tissue during the procedure. Additionally, ablation of cardiac tissue generates heat that can damage non-targeted adjacent tissues and coagulate blood. Consequently, adequate fluid irrigation of the ablation electrode is often required. Insufficient irrigation can result in off-target tissue damage and coagulation of blood, while excessive irrigation can result in inadequate ablation of the target tissue and also may result in delivery of excessive amounts of fluid to the patient's cardiovascular system, causing further adverse effects, particularly in patients who suffer from heart failure.

Accordingly, there remains a need for catheters having improved recording, electrical mapping, irrigation, and ablation abilities.

SUMMARY

Catheters having improved recording, electrical mapping, and irrigated ablation abilities are provided herein, as well as methods for treating tissue.

In one aspect, an ablation catheter is provided that includes an elongate body and an end effector. The elongate body has proximal and distal ends with an inner lumen extending there between. The end effector has a plurality of electrodes disposed thereon, and the end effector has first, second, and third configurations. In the first configuration, the plurality of electrodes is configured to be able to form a single point lesion and/or a linear lesion. In the second configuration, the plurality of electrodes is configured to be able to form a circumferential lesion. In the third configuration, the end effector is configured to stabilize at least one central electrode of the plurality of electrodes relative to a tissue surface.

The ablation catheter can have a number of variations. In one example, when the at least one central electrode of the plurality of electrodes is stabilized relative to the tissue surface, the at least one central electrode is configured to form a single point lesion, to form a wide area lesion, and/or to record signals for purposes of electrical mapping. In some examples, the end effector can have a plurality of wings, and each wing of the plurality of wings can have at least one electrode of the plurality of electrodes thereon. In another example, each wing can have at least one bend point that is configured to bend when the end effector moves from one configuration to another configuration, for example from the first configuration to the second configuration or from the second configuration to the third configuration. In one configuration, for example the third configuration, the wings can also be configured to stabilize contact of the central electrode with the tissue surface. The ablation catheter can also include a lasso extending distally from the end effector, and the lasso can be configured to expand and contract relative to a longitudinal axis of the end effector. The lasso can also have a second plurality of electrodes thereon.

In still another example, the plurality of electrodes can include a plurality of proximal electrodes that are adjacent to a proximal end of the end effector, can include the at least one central electrode that is adjacent to a distal end of the end effector, and can include a plurality of mid-electrodes positioned between the proximal and distal electrodes. In some examples, the plurality of mid-electrodes can face distally, such as in the third configuration. In some examples, such as in the third configuration, each of the mid-electrodes and the central electrode can be in contact with the cardiac tissue and can be configured to record electrical signals in order to map electrical activity and/or to ablate cardiac tissue. The plurality of proximal electrodes can also be configured to move radially outward relative to a longitudinal axis of the end effector when the end effector moves from the first configuration to the second configuration. In another example, at least one electrode of the plurality of proximal electrodes and the plurality of mid-electrodes can include an inner electrode and an outer electrode.

In one example, one or more of the plurality of electrodes can be configured to deliver at least one of radiofrequency (RF) energy, energy configured for electroporation (also known as pulsed field ablation), and/or pulses of a monophasic and/or biphasic configuration to tissue. The ablation catheter can also include irrigation tubing configured to supply irrigation fluid to the plurality of electrodes. In some examples, at least a first electrode of the plurality of electrodes can be configured to ablate tissue, and at least a second electrode of the plurality of electrodes can be configured to record electrical signals from tissue.

In another embodiment, an ablation catheter is provided that includes an elongate body and an end effector. The elongate body has a proximal end, a distal end, and an inner lumen extending therebetween. The end effector is at the distal end of the elongate body. The end effector has a plurality of proximal electrodes adjacent to a proximal end thereof, at least one distal electrode adjacent to a distal end thereof, and a plurality of mid-electrodes positioned between the proximal and distal electrodes. The end effector is also movable between first, second, and third configurations. In the first configuration, the end effector extends linearly along a longitudinal axis. In the second configuration, the plurality of proximal electrodes are positioned radially outward of the longitudinal axis of the end effector. In the third configuration, the plurality of mid-electrodes face distally and are positioned substantially within a plane extending perpendicular to the longitudinal axis.

The ablation catheter can have numerous variations. For example, the end effector can have a plurality of wings, and each wing can have at least one proximal electrode of the plurality of proximal electrodes and at least one mid-electrode of the plurality of mid-electrodes thereon. In another example, each wing can have at least one bend point that is configured to allow each wing to bend into the first, second, and third configurations. The ablation catheter can also include a lasso extending distally from the end effector, and the lasso can be configured to expand and contract relative to a longitudinal axis of the end effector. The lasso can also have a second plurality of electrodes thereon.

In another embodiment, an ablation catheter is provided that has an elongate body and an expandable end effector. The elongate body has proximal and distal ends with an inner lumen extending there between. The expandable end effector has a plurality of elongate members extending between a proximal end and a distal end of the end effector, and each elongate member is movable between a linear configuration and an expanded configuration in which the plurality of elongate members form a substantial sphere. Each elongate member includes a fluid channel extending therethrough and at least one electrode thereon, and a fluid reservoir is formed in the elongate member adjacent to each electrode for receiving fluid from the fluid channel.

A number of variations of the ablation catheter are possible. For example, the electrode can include at least one fluid lumen formed therethrough for releasing fluid from the fluid reservoir. In another example, each elongate member of the plurality of elongate members has at least a first bend point thereon. In still another example, the ablation catheter can also have a lasso extending distally from the end effector. The lasso can be configured to move between a compressed position and an expanded position, and the lasso can have at least a second electrode thereon. The ablation catheter can also have a removable sheath that is configured to compress the lasso in the compressed position, and the lasso can be biased to the expanded position. In still another example, the plurality of elongate members can be rotatable relative to the elongate body.

In another aspect, an ablation catheter is provided that has an elongate body, and expandable end effector, and first and second fluid reservoirs. The elongate body has proximal and distal ends with an inner lumen extending there between. The expandable end effector has a first electrode, a plurality of second electrodes, and a plurality of third electrodes. The first and second fluid reservoirs are formed between the elongate body and the expandable end effector. The first fluid reservoir is configured to deliver irrigation fluid to the plurality of second electrodes, and the second fluid reservoir is configured to deliver irrigation fluid to the plurality of third electrodes. A fluid pathway extends through the elongate body and is configured to deliver fluid to the first electrode.

The ablation catheter can have a number of different variations. For example, the end effector can be rotatable relative to the elongate body and relative to the first and second fluid reservoirs. In another example, the fluid pathway extends through the first and second fluid reservoirs. Each electrode of the plurality of second electrodes and the plurality of third electrodes can also have at least one chamber defined against an inner surface of the electrode and at least one irrigation port. The chamber can be configured to receive irrigation fluid, and the irrigation port can be configured to release irrigation fluid from the chamber to surrounding tissue. In still another example, the ablation catheter can include a rotational mechanism configured to allow the plurality of second electrodes and the plurality of third electrodes to rotate freely relative to a longitudinal axis of the elongate body. In some examples, the rotational mechanism is configured to allow more than 360 degrees of rotation. In some examples, the rotational mechanism can include a ring-shaped rotator and two tabs.

In still other examples, at least one of the first electrode, the plurality of second electrodes, and the plurality of third electrodes can be configured to deliver at least one of RF energy, energy configured for electroporation (also known as "pulsed field ablation"), and/or pulses of a monophasic and/or biphasic configuration. In some examples, at least one electrode of the first electrode, the plurality of second electrodes, and the plurality of third electrodes can be configured to ablate tissue, and at least another electrode of the first electrode, the plurality of second electrodes, and the plurality of third electrodes can be configured to record electrical signals from tissue.

In another embodiment, an ablation catheter is provided that includes an elongate body and an expandable end effector. The elongate body has proximal and distal ends with an inner lumen extending there between, and the distal end of the elongate body includes at least one fluid reservoir therein. The expandable end effector is rotatably coupled to the distal end of the elongate body and is movable between a linear configuration and an expanded configuration. The expandable end effector includes a plurality of electrodes and includes at least one fluid pathway extending therethrough. At least one fluid delivery tube extends between the at least one fluid reservoir and the at least one fluid pathway, and the at least one fluid delivery tube is configured to deform when the expandable end effector is rotated relative to the elongate body.

The ablation catheter can have a number of variations. For example, the at least one fluid delivery tube can include a proximal end coupled to the at least one fluid reservoir and a distal end coupled to the at least one fluid pathway. The distal end can be rotationally offset from the proximal end when the at least one fluid delivery tube is deformed. In another example, the end effector can be rotatable relative to the elongate body. In still another example, each electrode of the plurality of electrodes can have at least one chamber defined against an inner surface of the electrode and at least one irrigation port. The chamber can be configured to receive fluid from the at least one fluid pathway, and the irrigation port can be configured to release fluid from the chamber to surrounding tissue. In another example, the ablation catheter includes a rotational mechanism configured to allow the plurality of electrodes to rotate relative a longitudinal axis of the elongate body. At least one of the plurality of electrodes can also be configured to deliver at least one of RF energy, energy configured for electroporation, and/or pulses of a monophasic and/or biphasic configuration. In other examples, at least one of the plurality of electrodes can be configured to ablate tissue, and at least another electrode of the plurality of electrodes can be configured to record electrical signals from tissue.

In another aspect, a surgical device is provided that includes an elongate body, an end effector, and a handle assembly. The elongate body has a proximal end, a distal end, and an inner lumen extending between the proximal and distal ends. The end effector is coupled to the distal end of the elongate body and is movable between collapsed and expanded configurations. The handle assembly is coupled to the proximal end of the elongate body. The handle assembly includes an actuator that is operatively coupled to the end effector such that rotation of the actuator is effective to cause rotation of the end effector relative to the elongate body, and linear translation of the actuator is effective to move the end effector between the collapsed and expanded configurations. The actuator has predetermined fixed rotational positions, and a quantity of predetermined fixed rotational positions varies based on the linear position of the actuator.

The surgical device can have a number of variations. For example, the quantity of predetermined fixed rotational positions can increase as the actuator moves proximally. In another example, the end effector can be configured to move between the collapsed configuration, the expanded configuration, and a semi-expanded configuration. In still another example, channels in the handle assembly can define the predetermined fixed rotational positions of the actuator. The surgical device can also include a pin translatable within the channels in the handle assembly and that is configured to guide the actuator. In one example, at least one of the channels can have divots formed therein at predetermined distances within the channel. The end effector can also have a plurality of electrodes thereon. In some examples, the end effector can be configured to deliver energy to at least one of the electrodes. In other examples, the end effector can be configured to deliver irrigation fluid to at least one of the plurality of electrodes. In still other examples, the predetermined fixed rotational positions can be configured such that, with advancement to each successive rotational position, at least one of the plurality of electrodes that is in contact with tissue moves a predetermined fixed circumferential distance relative to the tissue.

In another embodiment, a surgical device is provided that includes an elongate body, an expandable end effector, and a handle assembly. The elongate body has a proximal end, a distal end, and an inner lumen extending between the proximal and distal ends. The expandable end effector is coupled to the distal end of the elongate body. The handle assembly is coupled to the proximal end of the elongate body. The handle assembly includes an actuator that is operatively coupled to the end effector such that rotation of the actuator is effective to cause rotation of the end effector relative to the elongate body and proximal translation of the actuator is effective to expand the end effector. Rotation of the actuator from a first position to a second rotated position will cause the actuator to translate distally by a predetermined distance and then translate proximally by the predetermined distance.

The surgical device can have numerous variations. For instance, rotation of the actuator from the first position to the second rotated position can also cause the actuator to rotate the end effector by a predetermined rotational distance. In another example, at least one channel in the handle assembly can define the first position and the second rotated position. In some examples, the at least one channel can have a plurality of rotation points therein, and the plurality of rotation points can be configured to define the first position and the second rotated position. In other examples, the at least one channel can have divots formed therein at predetermined distances within the channel. The surgical device can also include an actuation control mechanism that is configured to control rotation and translation of the actuator. In still another example, the end effector can have a plurality of electrodes thereon. In some examples, the end effector can be configured to deliver energy to at least one of the plurality of electrodes. The end effector can also be configured to deliver irrigation fluid to at least one of the plurality of electrodes. In still other examples, rotation of the actuator from a first position to a second rotated position can be configured to cause at least one of the plurality of electrodes that is in contact with tissue to move a predetermined fixed circumferential distance relative to the tissue.

In another aspect, a surgical device is provided that has an elongate body, an end effector, and a handle assembly. The elongate body has a proximal end, a distal end, and an inner lumen extending between the proximal and distal ends. The end effector is coupled to the distal end of the elongate body by a rotational mechanism that is configured to allow rotation of the end effector relative to the elongate body. The handle assembly is coupled to the proximal end of the elongate body, and the handle assembly has an actuator that is configured to control rotation of the end effector relative to the elongate body.

The surgical device can have a number of variations. For example, the end effector can be expandable, and the actuator of the hand assembly can be configured to control expansion of the effector. In another example, the end effector can have a plurality of electrodes thereon. In still other examples, the end effector can be configured to deliver energy to at least one of the plurality of electrodes. The end effector can be configured to deliver irrigation fluid to at least one of the plurality of electrodes. In some examples, rotation of the actuator from a first position to a second rotated position can be configured to cause at least one of the plurality of electrodes on the end effector to rotate a predetermined fixed circumferential distance relative to the elongate body, and the end effector can be configured to deliver energy and irrigation fluid to the plurality of electrodes.

BRIEF DESCRIPTION OF THE DRAWINGS

The invention will be more fully understood from the following detailed description taken in conjunction with the accompanying drawings, in which:

FIG. 1 is a perspective view of one embodiment of a catheter with a handle, an elongate body, and an end effector;

FIG. 7A is a simplified side view of the end effector of FIG. 7 within a pulmonary vein of a patient expanded to conform to the ostium;

FIG. 7B is a simplified side view of the end effector of FIG. 7;

FIG. 7C is a simplified top down view of a lesion pattern created by the end effector of FIG. 7;

FIG. 7D is a simplified top down view of an overlapping lesion pattern created by the end effector of FIG. 7 after rotation;

FIG. 7E is a simplified side view of another embodiment of an end effector of a catheter within a pulmonary vein of a patient expanded to conform to the antrum;

FIG. 7F is a simplified side view of the end effector of FIG. 7E within a pulmonary vein of a patient expanded to conform to the ostium;

FIG. 7G is a simplified side view of the end effector of FIG. 7E demonstrating varying degrees of radial expansion;

FIG. 10A is a simplified side view of the end effector of FIG. 8;

FIG. 10B is a simplified top down view of a lesion pattern formed by the end effector of FIG. 8 in one rotational position;

FIG. 10B1 is a simplified top down view of an overlapping lesion pattern formed by the end effector of FIG. 8 after two successive rotational positions;

FIG. 10C is a perspective view of the distal end of the catheter of FIG. 1 with one embodiment of an outer sheath assisting in transitioning the end effector from the first, linear configuration to the third, distally planar configuration;

FIG. 10D is a perspective view of the end effector and outer sheath of FIG. 10C during transition;

FIG. 10E is a perspective view of the end effector and outer sheath of FIG. 10C during transition;

FIG. 10F is a perspective view of the end effector and outer sheath of FIG. 10C during transition;

FIG. 10G is a perspective view of the end effector and outer sheath of FIG. 10C after transition to the third, distally planar configuration;

FIG. 11 is a top down view of one embodiment of a wing and a distal electrode of the catheter of FIG. 1 with the wing extended out;

FIG. 12 is a cross-sectional side view of the wing and the distal electrode of FIG. 11 taken along axis A2;

FIG. 13 is an enlarged cross-sectional side view of the wing taken at B in FIG. 12;

FIG. 16 is a cross-sectional side view of one embodiment of an electrode on the wing of FIG. 11;

FIG. 16A is a top-down view of another embodiment of an electrode;

FIG. 16B is a top-down view of another embodiment of an electrode;

FIG. 17 is a perspective, partially-transparent view of embodiments of a rotational mechanism, various irrigation tubes, and fluid reservoirs of the catheter of FIG. 1;

FIG. 18 is a perspective side view of the rotational mechanism of FIG. 17;

FIG. 24D is a screenshot of an animation of a split screen view of the end effector, the elongate body, and the handle of the catheter of FIG. 1 during an initial ablation of one example of a wide pulmonary vein;

FIG. 24E is a screenshot of an animation of the catheter of FIG. 24D during rotation of the end effector;

FIG. 24F is a screenshot of an animation of the catheter of FIG. 24D after a second ablation of the wide pulmonary vein;

DETAILED DESCRIPTION

Figure 3A:
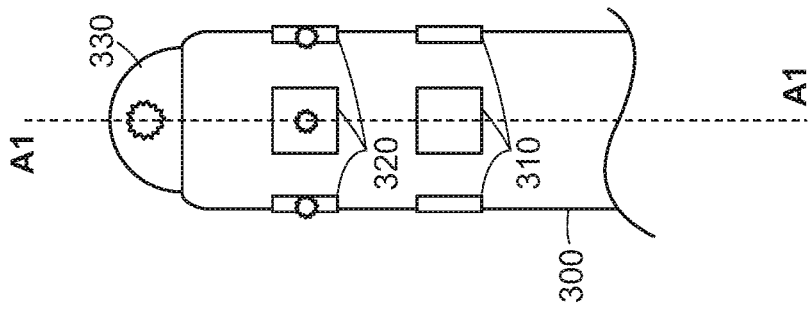
FIG. 3A is a simplified side view of the end effector of FIG. 2.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various catheters are provided herein that can effectively record and/or map electrical impulses in cardiac muscle and can ablate tissue through effective irrigation and energy application. Treatment of cardiac arrhythmias through use of tissue ablation often requires recording, mapping, and ablating one or more specific target sites within and around a heart of a patient, including on atrial walls and within pulmonary veins. As such, the catheters provided herein can be used to precisely locate the site(s) to be ablated and to confirm that ablation has been successful. These same catheters can also be used to effectively ablate target tissue to form lesions that can eliminate or isolate electrical impulses through the ablated tissue. As such, the catheters provided herein can simplify tissue ablation procedures, can reduce or eliminate requirements for additional catheters and/or excessive imaging equipment, can reduce or prevent recurrence of arrhythmia in patients, and can reduce or prevent the occurrence of adverse events resulting from off-target delivery of ablation energy or other causes.

In one exemplary embodiment, a catheter is provided that has a handle, an end effector with a plurality of electrodes, and an elongate body extending therebetween. The elongate body has a proximal end, a distal end, and an inner lumen, and the end effector is positioned at the distal end of the elongate body. The end effector has proximal electrodes, mid-electrodes, and at least one distal electrode. The proximal electrodes are adjacent to a proximal end of the end effector, the distal electrode is adjacent to a distal end of the end effector, and the mid-electrodes are positioned between the proximal and distal electrodes. The end effector is also movable between first, second, and third configurations. In the first configuration, the end effector extends linearly along a longitudinal axis thereof. In the second configuration, the plurality of proximal electrodes is positioned radially outward of the longitudinal axis. In the third configuration, the mid-electrodes face distally and are positioned substantially within a plane extending perpendicular to the longitudinal axis.

FIGS. 1-16 illustrate one embodiment of a catheter 10 that has a handle 100 on a proximal end, an end effector 300 on a distal end, and an elongate body 200 extending therebetween along a longitudinal axis A1 to connect the handle 100 and the end effector 300.

The end effector 300 is insertable into a body cavity of a patient to be positioned adjacent to and/or in contact with cardiac tissue to record and/or map electrical impulses in the cardiac tissue and to ablate target tissue, such as during treatment of atrial fibrillation. The illustrated end effector has a plurality of wings 302 that move between at least first, second, and third configurations, a plurality of electrodes 310, 320, one or more irrigation reservoirs 340, 342, a rotational mechanism 350, and a central tube 334 extending along the axis A1. Each wing 302 extends between the distal end of the end effector 300 and the rotational mechanism 350, and each wing has one or more proximal electrodes 310 positioned closer to a proximal end of the end effector 300, one or more mid-electrodes 320 positioned between the proximal electrodes 310 on the wing 3002, and flexible irrigation tubes extending therethrough, as discussed in detail below. A distal-most electrode 330 is positioned at the distal end of the end effector 300.

Figure 3:
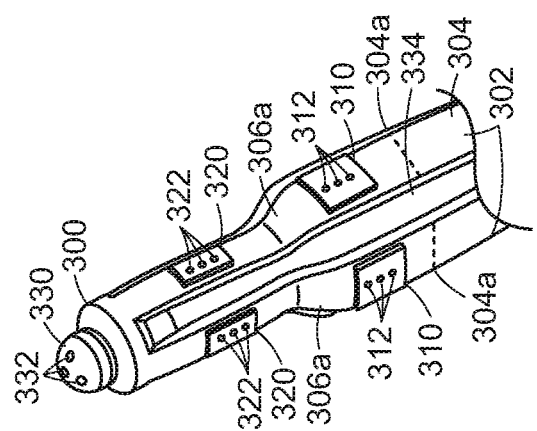
FIG. 3 is a perspective view of the end effector of FIG. 2.
Figure 2:
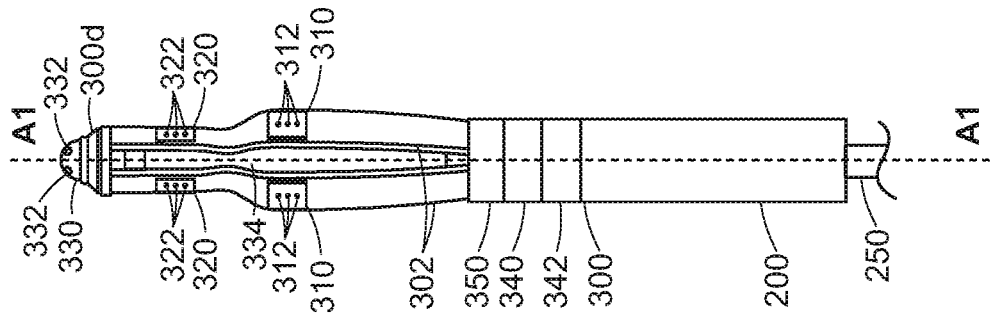
FIG. 2 is a side view of the distal end of the catheter of FIG. 1 with the end effector in a first, linear configuration.
Figure 4:
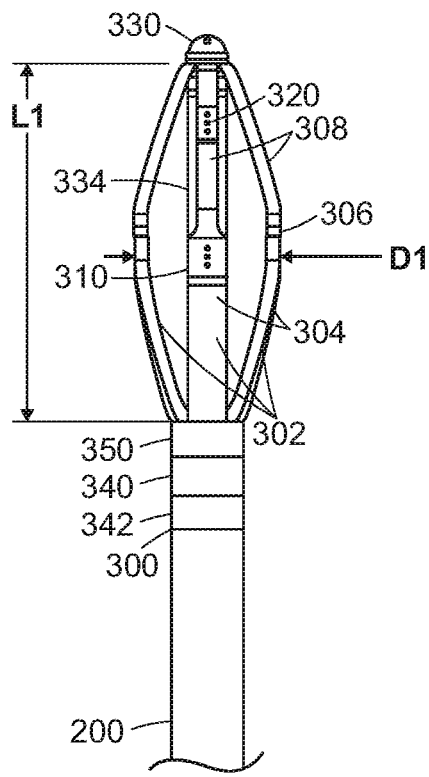
FIG. 4 is a side view of the distal end of the catheter of FIG. 1 with the end effector in a second, at least partially radially expanded configuration.

The wings 302 can have a first linear configuration, as illustrated in FIGS. 2-3A, which can be used, for example, to spot treat tissue. The wings 302 can have a second radially expanded configuration, as illustrated in FIGS. 4-7, which can be used, for example, to treat tissue encircling the end effector 300. The wings 302 can have a third distally planar configuration, as illustrated in FIGS. 8-10B, which can be used, for example, to treat a wider surface area of tissue. Additionally, the second radially expanded configuration can include a number of expanded positions between the first linear configuration and the third distally planar configuration. As such, the wings 302 on the end effector 300 create a flexible structure that can adapt to various shapes to ensure the electrodes can be positioned adjacent to relevant target tissue regardless of an anatomical shape of the target tissue, such as in a pulmonary vein or along an atrial wall. Additionally, the wings 302 can limit any occlusion of blood flow, such as blood flow through a pulmonary vein, to avoid various risks of clot formation and embolization and to avoid difficulties of positioning electrodes experiencing pressure buildup from occluded blood flow. While four wings are illustrated and discussed below, any number of wings can be used, such as between two and ten, and each wing can be made of a variety of different materials, such as plastics, elastomers, metal, various fibers, etc. The wings can have various electrical wires, irrigation tubing or channels, etc. extending therethrough, as discussed further below, and the wings can be made of one or more layers of various materials, such as flexible plastics, various polymers, metal and/or metal alloys, etc.

The plurality of wings 302 can transition between the first, second, and third configurations through use of a plurality of bend points, e.g., bend points 304a, 306a as shown, formed on each wing and an actuator 250 that extends between the end effector 300 and the handle 100. When the actuator is retracted proximally to a proximal-most position, the end effector 300 is in the first configuration. In the first configuration, the plurality of wings extend linearly along the axis A1 such that the proximal and mid-electrodes 310, 320 are generally aligned with and face perpendicularly away from the axis A1, as illustrated in FIGS. 2, 3, and 3A.

Figure 7:
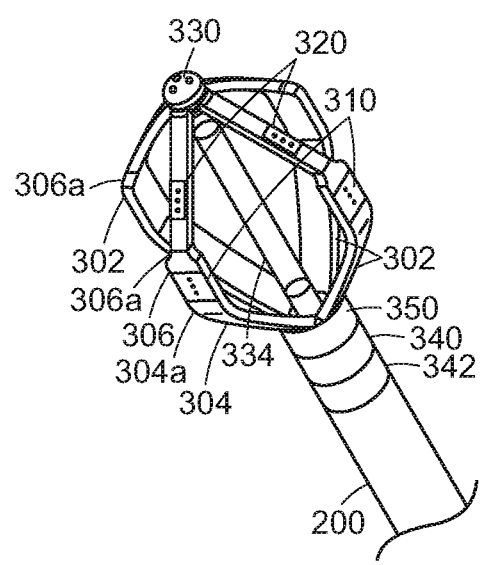
FIG. 7 is a perspective view of the end effector of FIG. 6.
Figure 10:
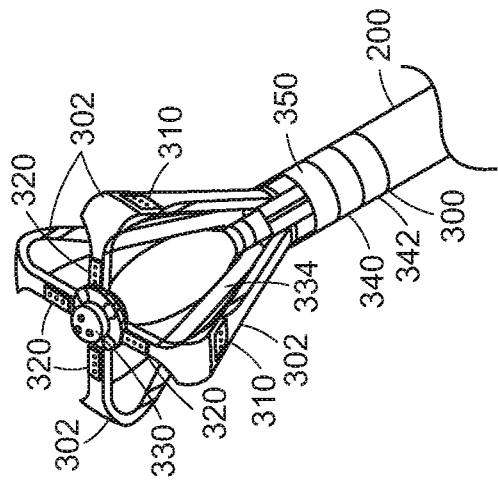
FIG. 10 is a perspective view of the end effector of FIG. 8.
Figure 9:
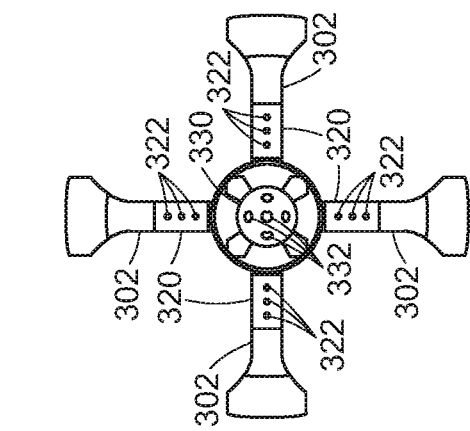
FIG. 9 is a top down view of the end effector of FIG. 8.

As the actuator 250 is advanced distally, the proximal end of each wing 302 is advanced distally relative to the distal end of the end effector, causing a mid-portion of each wing 302 to buckle or bend radially outward at the bend point away from the axis A1 and toward the second configuration. This forms a generally bowed or curved configuration. The proximal electrodes 310 thus move radially outward from the axis A1 while the mid-electrodes 320 are angled to at least partially face distally in the same direction as the distal electrode 330, as illustrated in FIGS. 4-7. At least first and second bend points 304a, 306a are formed on each wing 302, with the first bend point 304a positioned proximal to the proximal electrode 310 and the second bend point 306a positioned between the proximal and mid-electrodes 310, 320. As such, each wing 302 is divided into a proximal planar portion 304, a middle planar portion 306 with the proximal electrode 310 thereon, and a distal planar portion 308 with the mid-electrode 320 thereon. As each wing 302 is forced radially outward during transition, the first and second bend points 304a, 306a cause the wing 302 to bend at those points such that the middle portion 306 of the wing 302 with the proximal electrode 310 expands radially away from the axis A1. The middle portion 306 of the wing 302 continues to face perpendicularly or radially away from the axis A1, and the proximal and distal portions 304, 308 of the wing 302 extend at non-zero angles relative to the axis A1. Because the wings 302 are positioned equidistant from each other around the axis A1, the wings 302 form a three-dimensional shape similar to an octahedron or a substantially spherical shape in the second configuration. Because of the first and second bend points 304a, 306a on each wing 302, the shape formed by the wings 302 is especially effective at creating lesions at the ostium within a pulmonary vein of a patient, as illustrated in FIG. 7A and FIG. 7B. FIG. 7C shows ablation lesions 360 created by the electrodes 310 shown in FIGS. 7A and 7B when the end effector is in one rotational position. FIG. 7D shows overlapping ablation lesions created by the electrodes 310 after the end effector has been in two successive rotational positions 45 degrees apart, demonstrating how the overlapping lesions create a continuous circumferential ablation lesion that blocks electrical conduction in the tissue. However, in other embodiments, wings with a single bend point can be provided to more effectively create lesions at the antrum of the pulmonary vein (while also still being able to create lesions at the ostium). FIGS. 7E-7G illustrate another embodiment of an end effector 300a, similar to end effector 300, with a plurality of wings 302a and a plurality of electrodes 310a, 320a, 330a. Each wing 302a has a single bend point 304a positioned behind the corresponding proximal electrode 310a so that, as each wing 302a is advanced distally, the proximal electrodes 310a are angled to be especially effective at creating lesions in the antrum (as illustrated in FIG. 7E) while still being able to create lesions in the ostium (as illustrated in FIG. 7F). As shown in FIG. 7G, the single bend point 304a on each wing 302a allows a user to advance or retract an actuator to vary the angle of each wing 302a (and thus the electrode position relative to a center of the pulmonary vein) during use. This variability allows greater accommodation of pulmonary veins of different sizes.

Additionally, in the second configuration, the distance of radial expansion of each wing 302 perpendicularly from the axis A1 can vary during use by moving the actuator 250 further distally or proximally. For example, the wings 302 can transition from a length L1 along the axis A1 and a diameter D1 perpendicular to the axis A1 in FIGS. 4 and 5, to a shorter length L2 and a larger diameter D2 in FIGS. 6 and 7. The lengths and diameters can vary depending on the desired use, such as lengths between approximately 5 mm and 30 mm and more preferably between approximately 16 mm 20 25 mm, and diameters between approximately 4 mm and 25 mm and more preferably between approximately 8 mm and 20 mm. As such, the radial profile or size of the end effector 300 can be increased or decreased in the second configuration to accommodate anatomy of different dimensions, such as various pulmonary veins as discussed further below.

Figure 8:
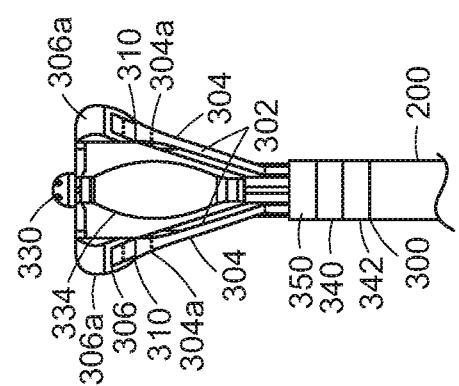
FIG. 8 is a side view of the distal end of the catheter of FIG. 1 with the end effector in a third, distally planar configuration.
Figure 14:
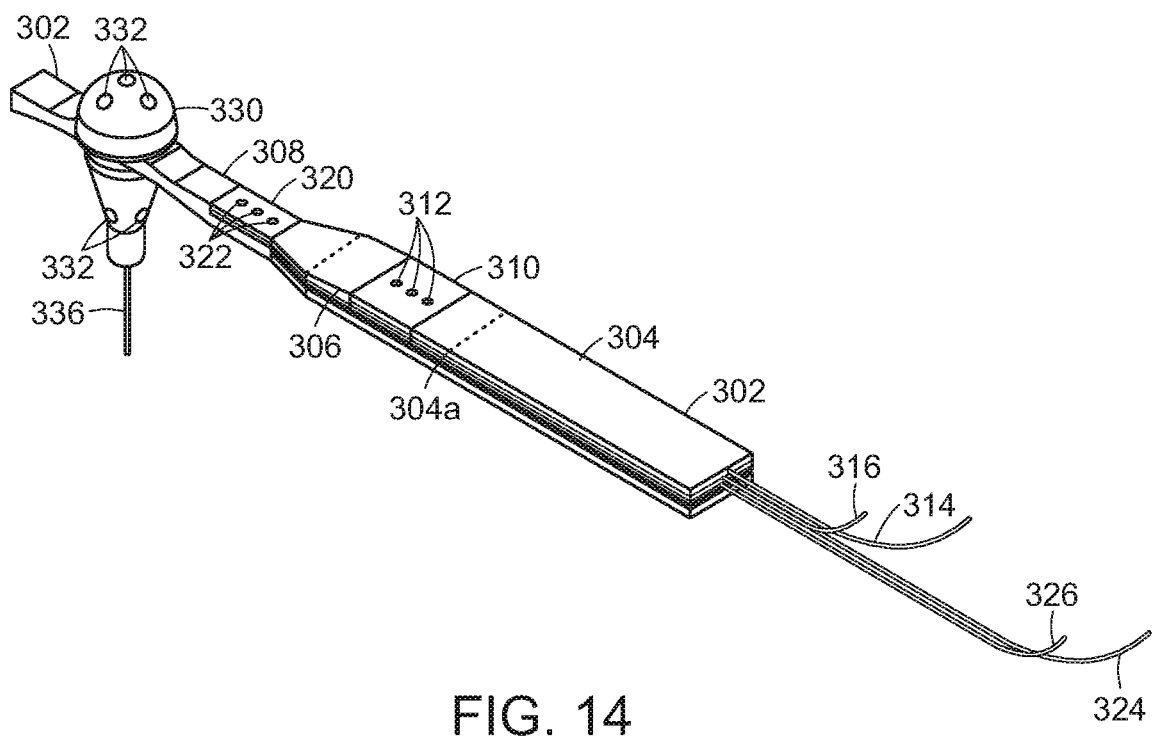
FIG. 14 is a perspective view of the wing and the distal electrode of FIG. 11 with the wing and various wires and irrigation tubes extended.

If the actuator 250 continues to be advanced distally, the end effector 300 transitions into the third configuration in which a portion of each wing 302 with the mid-electrode 320 transitions to face entirely distally. The second bend point 306a on each wing 302 continues to bend until the distal portion 308 of the wing 302 with the mid-electrode 320 faces entirely distally and is generally aligned with the distal electrode 330 in the third configuration. As such, the mid-electrodes 320 and the distal electrode 330 are positioned substantially within a plane extending perpendicular to the longitudinal axis A1, as illustrated in FIGS. 8-10B1, and can provide large surface areas of overlapping lesions 360 caused by ablative energy from the distal and mid-electrodes 320, 330, as illustrated in FIGS. 10B and 10B1. FIG. 10B demonstrates overlapping lesions created when the end effector is in one rotational position. FIG. 10B1 demonstrates overlapping lesions created after the end effector has been in two successive rotational positions 45 degrees apart. The proximal electrodes 310 are angled to face partially proximally away from the mid-electrodes 320 and the distal electrode 330 such that the end effector 300 forms a generally inverted four-sided pyramid shape. In this configuration, the first bend point 304a flattens so that the middle portion 306 of the wing 302 with the proximal electrode 310 generally aligns with the proximal portion 304 of the wing 302. The actuator 250 is discussed further below.

The bend points 304a, 306a are created by forming creases or notches in each wing 302 to cause bending at a particular point and under a particular amount of force applied by the actuator 250. In other embodiments, however, different shapes, bends, materials, etc. can be used to create different bend points. For example, the material used at a bend point can be of a different stiffness or flexibility than other material of the wing. Additionally, in some embodiments, the first and second bend points can be different from one another along each wing 302. For example, the second bend point can be more flexible or compliant while the first bend point can be stiffer or more resistant to bending to assist the end effector 300 to transition to the third configuration. In some embodiments, only one bend point or more than two bend points can be added per wing, such as between two and ten, to allow the plurality of wings to bend into different shapes.

In some embodiments, an outer sheath 270 around the elongate body 200 can be used to assist in transitioning between the first and third configurations. For example, the sheath 270 can be advanced distally along the elongate body 200 until encircling at least proximal-most portions of the wings 302 when the end effector 300 is in the first configuration, as sequentially illustrated in FIGS. 10C-10E. Once the sheath 270 is in place, as illustrated in FIG. 10E, the actuator 250 can be advanced distally to transition the wings 302 into the third configuration, as illustrated in FIGS. 10F and 10G. Because the sheath encircles the proximal-most portions of the wings 302, the end effector 300 can transition directly from the first to the third configuration, skipping the second configuration entirely.

As illustrated in FIGS. 11-16, each electrode 310, 320, 330 on the end effector 300 can selectively receive electrical impulses from a surrounding environment for use during recording and mapping, and it can selectively deliver ablation energy to target tissue adjacent to each electrode, as selected by a user. Various flexible conductive wires or thermocouples 316, 326, 336 can engage each electrode and extend proximally through the end effector 300, elongate body 200, and handle 100 to engage with a recordation source and/or a power source to record electrical impulses from the electrodes during recording and mapping and to deliver energy to the electrodes during ablation. Wires 316, 326 for each electrode 310, 320 positioned on one of the wings 302 can extend proximally through the wing 302, as illustrated in FIGS. 12 and 13, and the wires 336 for the distal electrode 330 can extend through a lumen of a central tube 334 that extends proximally along the axis A1, discussed further below. The electrodes 310, 320, 330 can receive one or more of a variety of different types of energy, such as radiofrequency (RF) energy, energy configured for electroporation (also known as pulsed field ablation), pulses of a monophasic and/or biphasic configuration, etc. Additionally, energy of each of these types can be delivered to each electrode relative to a different reference conductor. For example, each electrode can receive electrical energy relative to a grounding patch in contact with some region of the patient's body and/or relative to one or more other electrodes, between two electrodes on the same wing, etc. In some embodiments, the ability to deliver energy specifically between two electrodes on the same wing can be provided to create wider lesion rings around the pulmonary vein. While one distal electrode 330 is illustrated and each wing 302 is illustrated as having one proximal electrode 310 and one mid-electrode 320, any number of electrodes can be used at each location, such as between two and ten, etc., to allow for precise mapping and ablation energy delivery. For example, in some embodiments, one or more of the electrodes 310, 320, 330 can include two electrodes that are used for different purposes with a gap formed therebetween. As illustrated in FIG. 16A, a smaller inner electrode 338b can be used for recording and mapping, while a larger outer electrode 338a, by itself or in combination with inner electrode 338b, can be used for ablation (alone or in combination). The smaller size of the inner electrode 338b can provide for more precise recordation and higher signal resolution, which can be especially useful for purposes of electrical mapping. The larger size of the outer electrode 338a and/or the combination of electrodes 338a, 338b can be used for delivery of ablation energy to create larger ablation lesions and to manage current density more effectively, such as by allowing for lower current density. The gap formed between the inner electrode 338b and the outer electrode 338a can be calculated or sized to act as a short circuit for a high frequency signal used for ablation and open circuit for a low frequency signals recorded for purposes of electrical mapping. Another embodiment of a dual electrode arrangement is illustrated in FIG. 16B with a smaller inner electrode 338d and a larger outer electrode 338c that has a rectangular shape with rounded edges. However, a variety of different shapes can be used. A dual electrode approach can be especially beneficial for electrodes 320, 330 in the third configuration. Each electrode 310, 320, 330 can be made from various conductive materials, such as platinum, gold, etc. As illustrated in FIGS. 11-16, the proximal and mid-electrodes 310, 320 are generally rectangular, and the distal electrode 330 is generally dome or tear-drop shaped. However, a variety of different shapes can be used, such as oval, circular, triangular, etc.

Figure 15:
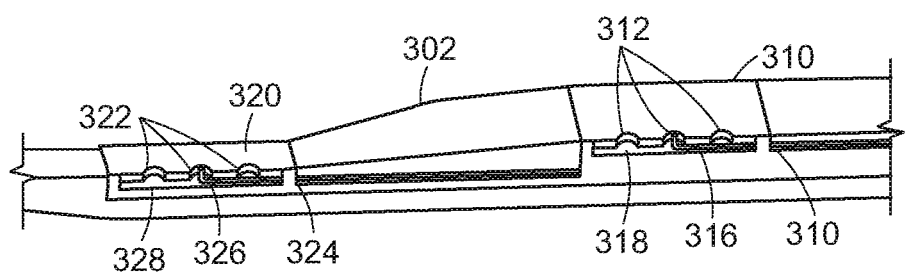
FIG. 15 is a cross-sectional perspective view of part of the wing of FIG. 11.
Figure 19:
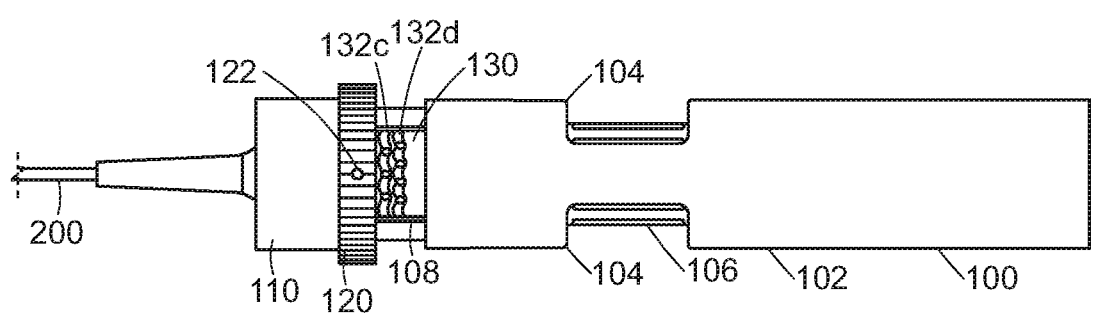
FIG. 19 is a side view of the handle and elongate body of FIG. 1.

Each electrode 310, 320, 330 is also irrigated by one or more flexible irrigation tubes 314, 324, 334 and irrigation ports 312, 322, 332 during ablation to avoid charring and burning of tissue being ablated. As illustrated in FIGS. 11-16, each proximal and mid-electrode 310, 320 has at least one tube 314, 324 for irrigation fluid extending between the proximal end of the end effector 300 and the electrode 310, 320 through each wing 302. The central tube 334 extends along the axis A1 and delivers irrigation fluid to the distal electrode 330, either directly through the lumen of the central tube 334 or through one or more dedicated irrigation tubes therein. The central tube 334 is discussed further below. The fluid for each proximal and mid-electrode 310, 320 on each wing 302 can be delivered to a chamber 318, 328 defined against an inner surface of the electrode, as illustrated in FIGS. 15 and 16, and each electrode can have one or more irrigation ports 312, 322 formed therethrough that allow irrigation fluid in each chamber to flow through the electrode and out to the surrounding environment. The chamber 318, 328 and irrigation ports 312, 322 allow fluid to disperse more freely between the electrode and any target tissue, which can allow more effective cooling and a more even distribution of irrigation fluid to the target tissue as opposed to a more directional or localized delivery that may occur if irrigation tubes are connected directly to the irrigation ports in the electrodes.

The irrigation tubes 314, 324 extend proximally to one or more fluid reservoirs 340, 342 on a proximal end of the end effector 300. The fluid reservoirs 340, 342 act to deliver irrigation fluid during ablation, to assist in maintaining appropriate fluid pressure, and to assist during rotation of the end effector, as discussed below. The fluid reservoirs 340, 342 receive irrigation fluid from one or more proximal infusion tubes 214, 224 that extend proximally from the fluid reservoirs 340, 342, through the elongate body 200 and the handle 100, and engage with one or more irrigation fluid sources. As illustrated in FIG. 17, the end effector 300 has first and second reservoirs 340, 342, and each reservoir has four irrigation tubes 314, 324 extending distally therefrom. Each of the irrigation tubes 324 from the first reservoir 340 extends distally through a corresponding wing 302 to a corresponding mid-electrode 320, and each of the irrigation tubes 314 from the second reservoir 342 extends distally through a corresponding wing 302 to a corresponding proximal electrode 310. Furthermore, as illustrated in FIG. 17, an elongate tube 234 extends within the elongate body 200 between the handle 100 and the end effector 300 along the axis A1, and it extends through the first and second reservoirs 340, 342 and engages the central tube 334 of the end effector 300 to provide passage of the wires 314, 324, 336 for the electrodes and any sensors and to provide fluid flow to the central tube 334. Additionally, in some embodiments, the first and second reservoirs 340, 342 can also be considered to be part of the elongate body 200 and separate from the end effector 300.

The central tube 334 of the end effector 300 extends along the axis A1 from the proximal end of the end effector 300 to the distal electrode. The central tube 300 has a fluid sealed lumen through which irrigation fluid can flow and through which sealed wiring can extend to the distal electrode 300. While the illustrated tube has one lumen, a plurality of fluid sealed lumens for delivery of irrigation fluid and/or fluid sealed lumens for wiring can extend therethrough. Furthermore, one or more additional wires can extend therethrough for sensors embedded in or around the end effector 300, such as a temperature sensor. Additionally, the central tube 334 can be expandable and contractible to expand radially outward in a direction perpendicular to the longitudinal axis A1 as the end effector 300 transitions from the first to the third configuration, as illustrated in FIGS. 2-10. The central tube 334 can also be made of a variety of materials, such as plastics, metals, elastomers, various woven plastic and/or metal fibers, etc. In some embodiments, the central tube 334 can be made from a flexible braid, such as flexible metal braids, that can cover all or a portion of the distal electrode 330 and the wiring 336 not in direct contact with or directly adjacent to tissue and thereby can serve as a Faraday cage, blocking energy being delivered to the distal electrode 330 from spreading to blood and tissue not in directly adjacent to the distal electrode. Such a spread of energy to non-targeted regions can potentially be undesirable from efficacy, efficiency, and patient safety perspectives. In some embodiments, the various fibers can also be coated with a flexible sealing material so that fluid does not pass through a wall of the tube. Additional examples of materials and embodiments of expandable and contractible housings can be found in U.S. Pat. No. 10,485,611 to Haghighi-Mood et al., filed on Sep. 24, 2018 and entitled "Catheter and Method for Improved Irrigation" and U.S. Pat. No. 9,717,558 to Desai, filed Nov. 7, 2017 and entitled "Catheter and Method for Improved Ablation," both of which are incorporated herein by reference in their entirety.

Figure 5:
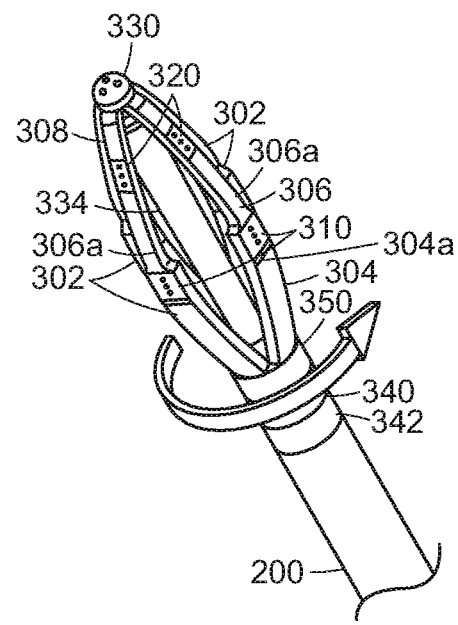
FIG. 5 is a perspective view of the end effector of FIG. 4 and illustrates rotation of the end effector.
Figure 6:
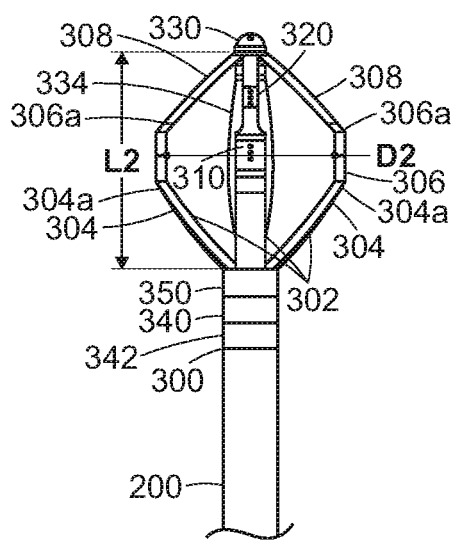
FIG. 6 is a side view of the end effector of FIG. 4 in the second configuration with greater radial expansion.

The end effector 300 can also have a rotation mechanism 350 that allows the end effector 300 to rotate at least partially about the axis A1. During use, the actuator 250 can be rotated by a user to cause rotation of the end effector 300 about the rotation mechanism 350 to allow the proximal and mid-electrodes 310, 320 to be rotationally repositioned in a body of a patient without having to rotate the entire elongate shaft 200. As discussed further below regarding the handle 100, the rotational functionality can allow a total number of wings and electrodes to be minimized while still creating overlapping lesions when ablating encircling tissue, such as in pulmonary veins. Use of fewer wings and electrodes provides a number of advantages. Reducing the number of wings reduces corresponding components on each wing and makes manufacturing easier. Using fewer wings and electrodes also allows the maximum diameter of the catheter 10 in the first configuration to be reduced, such as being 12 French or less, which makes introduction and manipulation of the end effector 300 easier and safer. Additionally, because fewer electrodes are needed due to the rotation mechanism 350, larger electrodes can be used to create larger lesions and to reduce risks of charring tissue or creating steam pops associated with use of smaller electrodes, and a smaller number of wires will be needed. As such, the catheter can accommodate higher gauge wires and thicker insulation for those wires while maintaining an acceptable diameter. Using larger electrodes and/or higher gauge wires with better insulation, in turn, allow for the use of higher voltage electrical pulses that can create adequately deep ablation lesions with a pulsed field (electroporation) technique. Fewer electrodes also allows for simpler irrigation of electrodes in each wing because fewer irrigation channels can be used while still maintaining effective irrigation, allowing for a smaller diameter and simpler manufacturing. The overall smaller size and fewer structural elements also provides for more flexibility in the end effector and wings to conform to pulmonary vein anatomy, which enables more precise and predictable lesion overlap. As illustrated in FIG. 5, the rotation mechanism 350 engages and is positioned between the reservoirs 340, 342 and terminal ends of the wings 302. As such, the wings 302 rotate relative to the reservoirs 340, 342 and the elongate body 200, and the irrigation tubes 314, 324 extending through the wings 302 to the proximal and mid-electrodes 310, 320 are partially rotated. However, because the irrigation tubes 314, 324 extend a relatively short distance to the fluid reservoirs 340, 342 rather than entirely through the elongate body 200, they can experience reduced or eliminated twisting or kinking during rotation. As illustrated in FIGS. 17 and 18, the rotation mechanism 350 is a ring-shaped rotator with two tabs 350*t* positioned opposite each other and extending proximally, and the tabs 350*t* on the rotation mechanism 350 engage slots or channels in the first reservoir 340. However, a variety of different rotation mechanisms can be used, such as ball bearings, grooves, various ball and joint mechanisms, threading, helical spirals, nut and bolt mechanisms, etc. Additionally, the rotation mechanism 350 can rotate freely about the axis A1, e.g. greater than 360 degrees, while rotation of the end effector 300 is limited by the handle 100 and/or irrigation tubing and wiring, as discussed below. However, in other embodiments, the rotation mechanism can limit rotation, such as to less than 360 degrees about the axis A1, less than 90 degrees about the axis A1, etc. In some embodiments, for end effectors containing four wings characterized by equal angular spacing between wings, rotations of greater than 90 degrees are often not required.

As indicated above, the catheter includes an elongate body 200. The proximal end of the end effector 300 can engage the distal end of the elongate body 200, and the elongate body 200 extends proximally to the handle 100. The elongate body has one or more lumens extending therethrough to allow passage of the various infusion tubes 214, 224, wires, the actuator 250, the elongate tube 234, etc., between the end effector 300 and the handle 100. Additionally, the elongate body 200 can incorporate one or more known steering mechanisms therein, such as through use of various cables, guidewires, etc.

As illustrated in FIGS. 19-24J, the handle 100 is positioned on the proximal end of the elongate body and controls movement of the end effector 300 within a patient, as well as transition of the end effector 300 between the first, second, and third configurations. The handle 100 has a body 102, an actuation control mechanism 110, and various irrigation fluid tubes and electrical wires extending through a lumen therein along the axis A1. The body 102 has a plurality of openings 104 defined therein to access an elongate body steering mechanism 104 such that rotation of the mechanism 106 allows steering of the elongate body, as illustrated in FIGS. 23A and 23B and as known in the art. The body 102 also defines a window 108 at a distal end with first and second sides 108*a*, 108*b* formed around a plurality of grooves or channels of the actuation control mechanism 110, discussed below. The actuator 250 engages with and extends distally from the body 102, and the actuator 250 is a hollow wire, however other structures can be used, such as rods, tubes, etc.

The actuation control mechanism 110 can be used to control rotation of the end effector 300 and to control transition of the wings 302 of the end effector 300 between the first, second, and third configurations. When in the second configuration, the actuation control mechanism 110 can also control an extent or radial expansion of the wings 302 to one or more predetermined configurations. In the illustrated embodiment, the actuation control mechanism 110 is arranged on a distal end of the handle 100, and it has a rotatable hub 120 and a cylindrical panel 130. The rotatable hub 120 has an annular cross-section with the elongate body 200, actuator 250, and various tubes and wires extending therethrough along the axis A1, and it encompasses a distal end of the cylindrical panel 130. The hub 120 is rotatable about the axis A1 around the panel 130 and is translatable along the axis A1 with respect to the panel 130. The hub 120 has a spring-biased pin 122 that protrudes radially inward toward the axis A1, and the panel 130 has a plurality of grooves or channels 132a, 132b, 132c, 132d on an outward-facing surface that are exposed by the window 108 of the housing 102 and that receive the pin 122 therein.

Figure 23B:
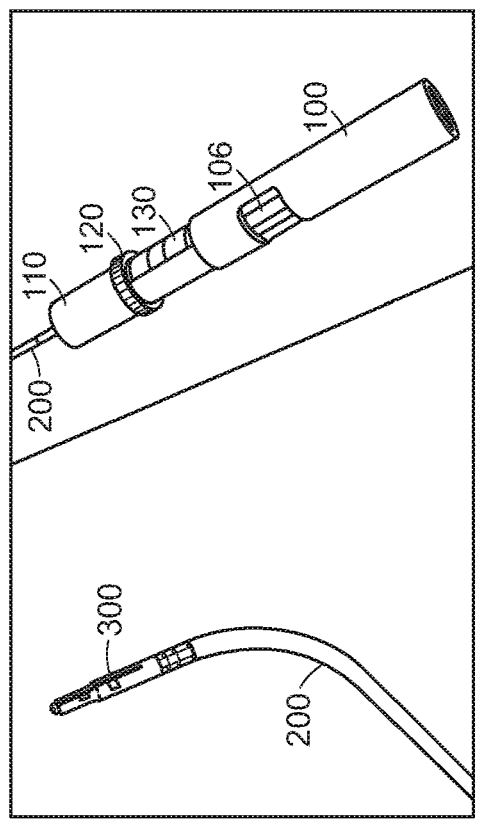
FIG. 23B is a screenshot of the animation of the catheter of FIG. 23A after steering of the elongate body.
Figure 23A:
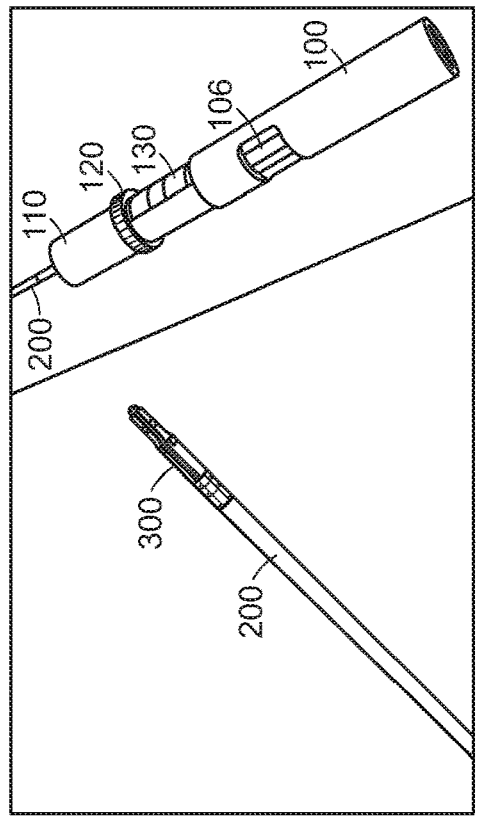
FIG. 23A is a screenshot of an animation of a split screen view of the end effector, elongate body, and the handle of the catheter of FIG. 1 before steering of the elongate body.

When the end effector 300 is in the first configuration, the hub 120 is in a distal-most position relative to the actuator 250 and the panel 130, as illustrated in FIGS. 23A and 23B. To transition the end effector 300 to the second configuration, the hub 120 is retracted proximally relative to the actuator 250 and the panel 130, and the pin 122 is brought into engagement with the grooves 132a, 132b, 132c, 132d, as discussed below. To continue transitioning the end effector 300 into the third configuration, the hub 120 is retracted to a proximal-most position relative to the actuator 250 and the panel 130.

Figure 24A:
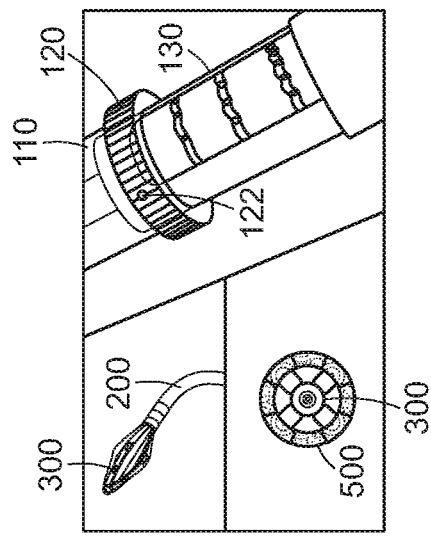
FIG. 24A is a screenshot of an animation of a split screen view of the end effector, the elongate body, and the handle of the catheter of FIG. 1 during an initial ablation of one example of a narrow pulmonary vein.
Figure 24C:
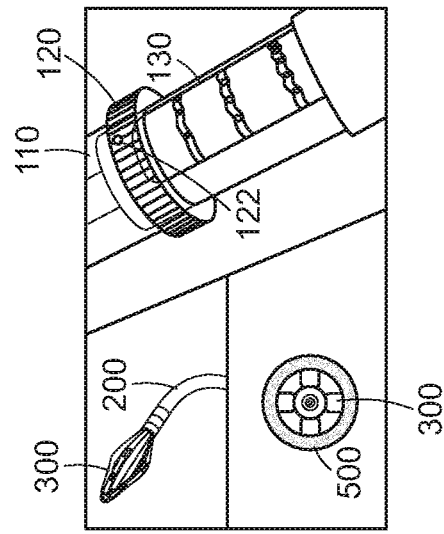
FIG. 24C is a screenshot of an animation of the catheter of FIG. 24A after a second ablation of the narrow pulmonary vein.
Figure 24B:
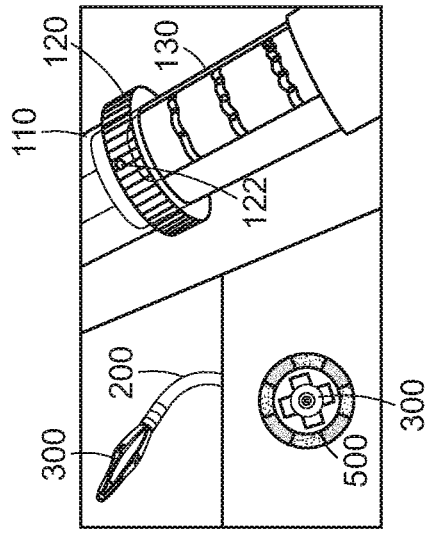
FIG. 24B is a screenshot of an animation of the catheter of FIG. 24A during rotation of the end effector.
Figure 24G:
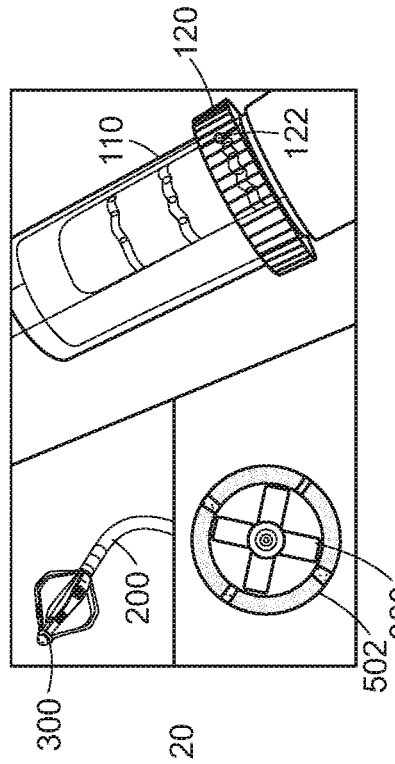
FIG. 24G is a screenshot of an animation of the catheter of FIG. 24D during rotation of the end effector.
Figure 24H:
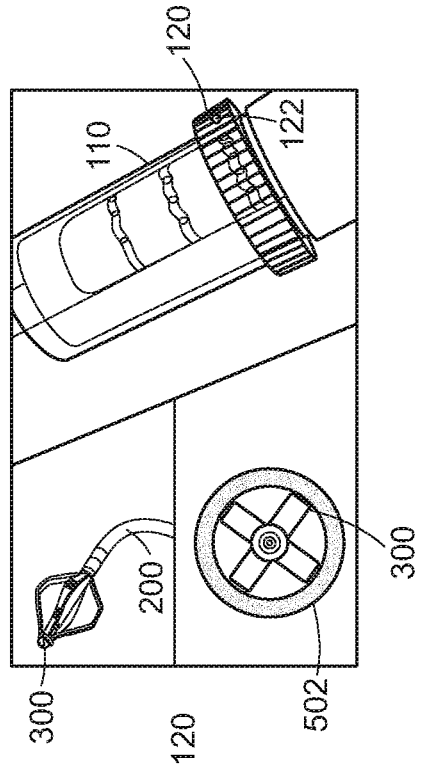
FIG. 24H is a screenshot of an animation of the catheter of FIG. 24D after a third ablation of the wide pulmonary vein.
Figure 24I:
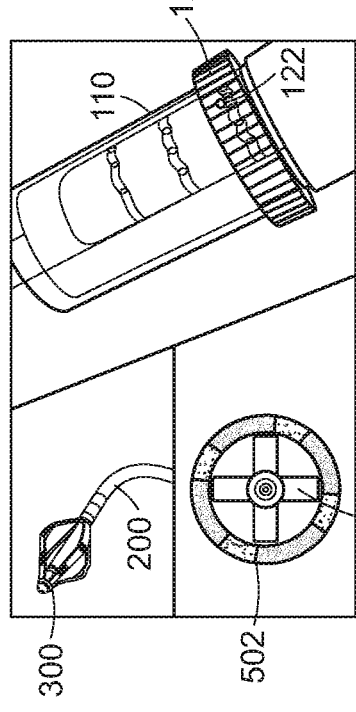
FIG. 24I is a screenshot of an animation of the catheter of FIG. 24D during rotation of the end effector.
Figure 24J:
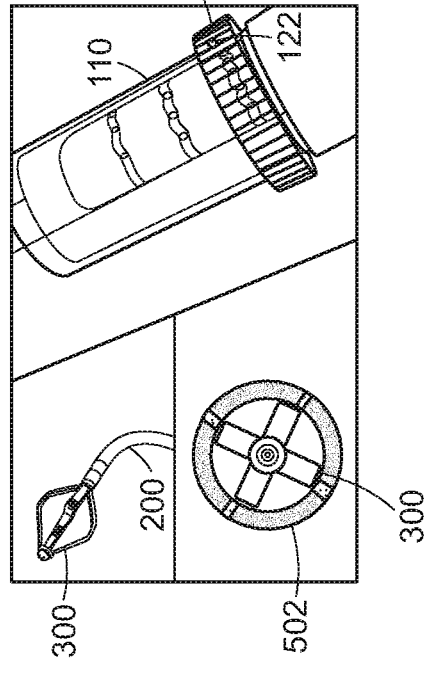
FIG. 24J is a screenshot of an animation of the catheter of FIG. 24D after a fourth ablation of the wide pulmonary vein.

First, second, third, and fourth grooves 132a, 132b, 132c, 132d are arranged parallel to each other and sequentially extending along the panel 130 perpendicular to the axis A1. The user begins to transition the end effector 300 from the first configuration to the second configuration by retracting the hub 120 proximally relative to the actuator 250 and the panel 130 to cause the pin 122 to engage the first groove 132a, resulting in the wings 302 expanding radially to the first distance D1, as illustrated in FIGS. 24A-24C. To continue to expand the wings 302 radially to a greater distance, such as distance D2, the user can continue to retract the hub 120 proximally relative to the actuator 250 and the panel 130, causing the pin 122 to sequentially engage the second, third, and fourth grooves 132b, 132c, 132d. Thus, as the rotatable hub 120 and pin 122 continue to progress proximally along the panel 130, the amount of radial expansion of the wings 302 continues to increase, for example as illustrated in FIGS. 24D-24J in which the pin 122 engages the fourth groove 132d.

Figure 20:
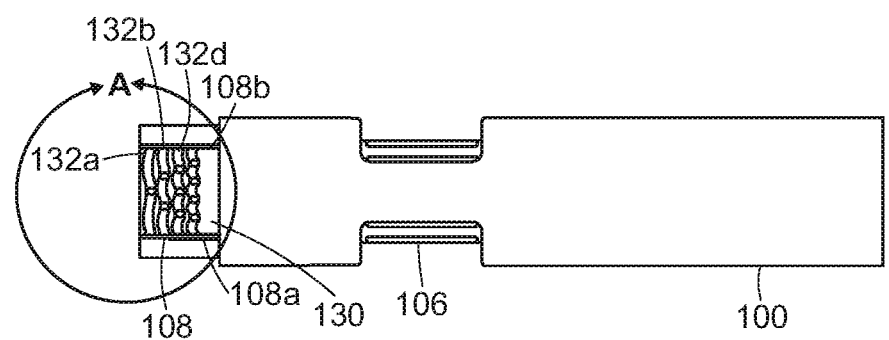
FIG. 20 is a side view of the handle of FIG. 19.
Figure 22:
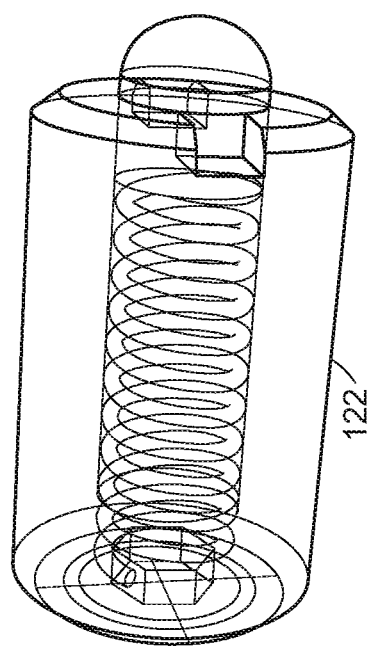
FIG. 22 is a perspective, partially transparent view of one embodiment of a pin in the handle of FIG. 19.
Figure 21:
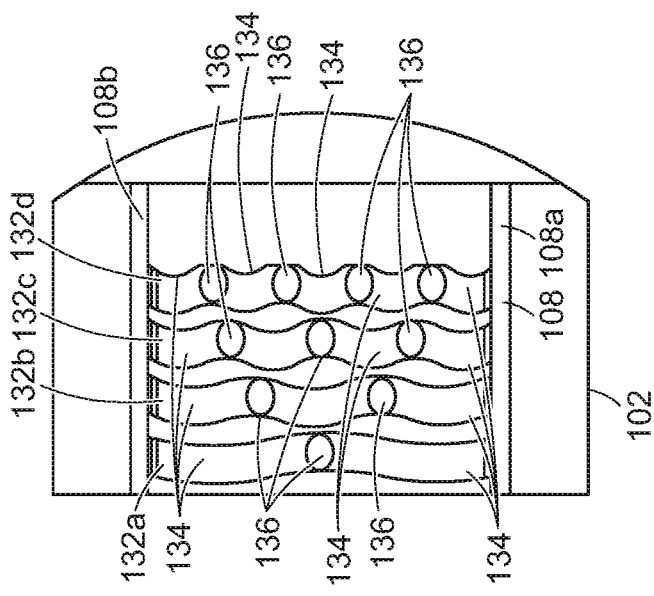
FIG. 21 is an enlarged side view of the handle taken at A in FIG. 20.

Each groove 132a, 132b, 132c, 132d extends a total of approximately 90 degrees around the outer perimeter of the cylindrical panel 130 between the first side 108a and the second side 108b of the window 108. Additionally, each groove includes one or more curves or bumps 134 formed therealong and one or more divots 136 formed in each groove 132a, 132b, 132c, 132d. For example, as illustrated in FIGS. 20 and 21, the first groove 132a is formed from first and second curves 134 with a first divot 136 formed therebetween. The first divot 136 formed approximately halfway along the groove 132a, or at a point approximately 45 degrees around the outer perimeter relative to the first side 108a or the second side 108b of the window 108. As such, when the pin 122 is in engagement with the first groove 132a and the end effector 300 is in the second configuration, the pin 122 allows guided rotation of the rotatable hub 120 relative to the actuator 250 and panel 130 within the first groove 132a. As the rotatable hub 120 is rotated and the pin 122 slides along the first groove 132a, the pin 122 translates distally by a predetermined distance relative to the actuator 250 and then translates proximally by the same predetermined distance as it translates across the first curve 134, as sequentially illustrated in FIGS. 24A-24C. This guided proximal and distal movement during rotation is mimicked by movement of the handle 100 and actuator 250 relative to the rotatable hub 120, causing the actuator 250 to retract slightly proximally and rotate as the pin 122 traverses the first curve 134 before advancing slightly distally during continued rotation and then being held still when the pin 122 engages the first divot 136. Corresponding movement of the end effector 300 occurs while the actuator 250 rotates and translates, causing the wings 302 to radially contract as the end effector 300 rotates and the pin 122 translates across the first curve 134 before radially expanding as the pin 122 engages the first divot 136. As such, if the end effector 300 is positioned in a passage or opening and is engaged with tissue for ablation, the wings 302 can radially contract during rotation to prevent the wings 302 from scraping or dragging along tissue and can radially expand when being re-positioned for ablation, as sequentially illustrated in FIGS. 24A-24C showing the when the pin 122 is engaged in the first groove 132a and as sequentially illustrated in FIGS. 24D-24J when the pin 122 is engaged in the fourth groove 132d.

Additionally, the number of curves and divots can be selected to ensure effective tissue ablation around an entire encircling tissue surface. For example, in a narrower passage or opening 500, as illustrated in FIGS. 24A-24C, the pin 122 can engage the first groove 132a to result in a narrower radial expansion of the wings 302 to position the proximal electrodes 310 adjacent to target tissue to be ablated 500. To ensure effective tissue ablation, the pin 122 can engage the first groove 132 adjacent to the first side 108a of the window 108, and the user can deliver an initial application of ablation energy, as illustrated in FIG. 24A. The user can then rotate the rotatable hub 120 approximately 45 degrees around the axis A1, as illustrated in FIG. 24B, guided by movement of the pin 122 in the first groove 132a to control an amount of rotation and to cause the wings 302 to contract during rotation. The user can then deliver a second application of ablation energy after the pin 122 engages the first divot 136, as illustrated in FIG. 24C. Because there are four proximal electrodes 310, this rotation results in ablation of tissue every 45 degrees around the encircling tissue 500, which can effectively cause overlapping ablation areas and effectively ablate all encircling tissue in a narrow passage.

In a wider passage or opening, a wider radial expansion of the wings 302 is required to position the proximal electrodes 310 adjacent to target tissue, and ablation of tissue every 45 degrees around the encircling tissue may not create overlapping ablation areas. As such, one of the second, third, or fourth grooves 132b, 132c, 132d can be selected, causing greater radial expansion of the wings 302. Additionally, each groove 132b, 132c, 132d can contain a correspondingly greater number of curves 134 and divots 136, resulting in guided application of energy a correspondingly greater number of times. For example, the second groove 132b has three curves 134 with two divots 136 between the curves 134, resulting in the divots 136 being positioned at approximately 30 degrees and approximately 60 degrees around the outer perimeter of the panel 130. Thus, encircling tissue in a wider passage can be entirely ablated through an initial application of ablation energy, through a second application of ablation energy after the rotatable hub 120 is rotated approximately 30 degrees and the pin 122 engages the first divot 136, and through a third application of ablation energy after the rotatable hub 120 is rotated another approximately 30 degrees and the pin 122 engages the second divot 136. Because there are four proximal electrodes 310, this rotation results in ablation of tissue every 30 degrees around the encircling tissue, which can effectively cause overlapping ablation areas and effectively ablate all encircling tissue in the passage. The third groove 132*c* has four curves 134 with three divots 136 formed therebetween, allowing greater radial expansion of the wings 302 and guided rotation and energy application at approximately every 22.5 degrees around the encircling tissue. The fourth groove has five curves 134 with four divots 136 formed therebetween, allowing even greater radial expansion of the wings and energy application at approximately every 18 degrees. As shown sequentially in FIGS. 24D-24J, encircling target tissue 502 is thus ablated four times by each proximal electrode 310 to create overlapping lesions on the tissue 500 entirely encircling the end effector 300. As such, the increased number of guided energy applications ensures that areas of overlapping ablated tissue are created even in larger passageways. As indicated above, each of the four grooves extends approximately 90 degrees around the outer perimeter of the panel 130, thus limiting a total rotational amount of the end effector 300 to approximately 90 degrees or less. Because there are four proximal electrodes 310 positioned every 90 degrees around the axis A1, rotation beyond 90 degrees is not required to ensure complete ablation of encircling target tissue. Additionally, limiting a total amount of rotation can help reduce or prevent pinching or kinking of the irrigation tubes and strain on wires in the end effector 300. The actuation control mechanism 110 can thus serve to simplify and automate the rotation and ablation process to provide more effective target tissue ablation. For example, the actuation control mechanism 210 can provide discrete angular rotations, and these rotations can be automatically adjusted to provide a reasonably constant linear separation between a previous and new location of the proximal and mid-electrodes 310, 320 during use to create overlapping lesions. Thus, many embodiments that have fixed rotational positions of an actuator can be configured so that, for each linear position of the actuator, an electrode located on a wing of an end effector and in contact with tissue can move a same fixed predetermined circumferential distance relative to tissue with which the electrode is in contact. Such movement can be caused with advancement to each successive rotational position of the actuator, and successive overlapping ablation lesions can be formed by the electrode in the tissue upon advancement to each successive rotational position.

Figure 27:
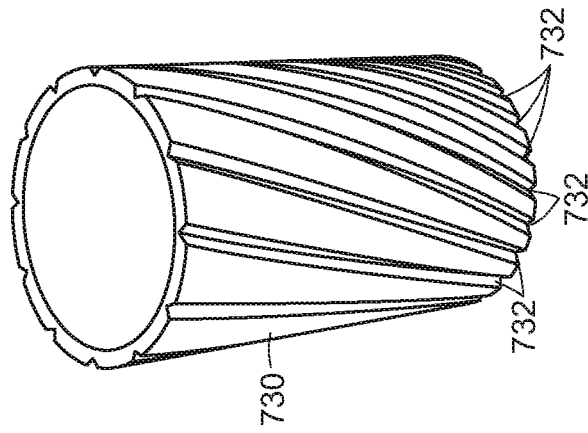
FIG. 27 is a perspective view of another embodiment of a cylindrical panel.
Figure 25:
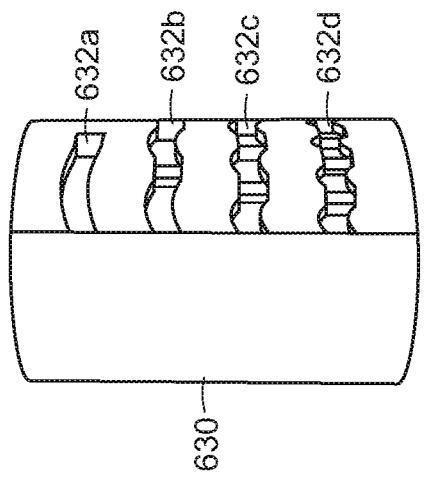
FIG. 25 is a side view of another embodiment of a cylindrical panel.
Figure 26:
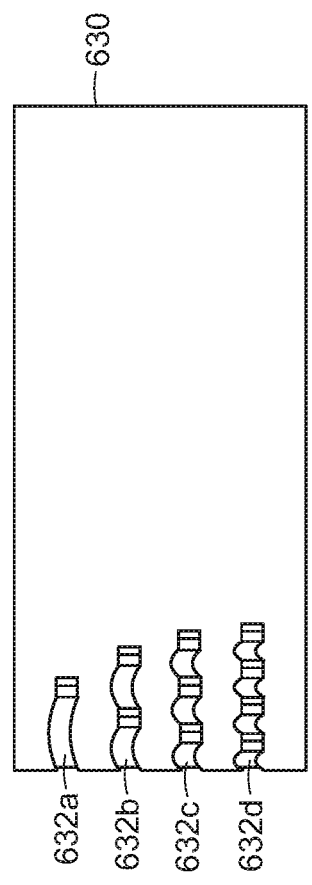
FIG. 26 is a side view of the cylindrical panel of FIG. 25 in a flattened or unrolled state.

While specific grooves, curvatures, and divots are illustrated, a variety of other embodiments are possible. For example, FIGS. 25 and 26 illustrate another embodiment of a cylindrical panel 630 similar to panel 130. The cylindrical panel 130 has four grooves 632*a*, 632*b*, 632*c*, 632*d* with curves and divots therein. However, the divots are arranged after each curve so that, for example, the first groove 632*a* limits a total rotation of the end effector 300 about the axis A1 to approximately 45 degrees by having only a first curvature and a first divot. As such, similar functionality to the cylindrical panel 130 above can be achieved while preventing any rotation beyond 45 degrees. Similarly, the second groove 632*b* limits total rotation of the end effector to approximately 60 degrees, the third groove 632*c* limits rotation to approximately 67.5 degrees, and the fourth groove 632*d* limits rotation to approximately 72 degrees. However, in other embodiments, a different number of grooves can be provided, such as between one and ten, and a different number of curves and divots can be provided, such as between one and 50, to vary a distance of radial expansion of the wings and a number of guided energy applications. In some embodiments, a divot can be formed at each rotational point of recommended energy application, including an initial rotational position. Additionally, an amount of curvature in each of the curves can be varied depending on how much radial contraction is desired during rotation, and a length of each groove along the outer perimeter of the panel can be varied to allow a greater or lesser amount of end effector rotation. For example, if a different number of wings is used, more or less total rotation may be preferable. Furthermore, as illustrated in FIG. 27, another embodiment of a cylindrical panel 730 similar to panel 130 can be provided with continuous grooves 732 extending diagonally along an outer surface of the panel 730 from a distal end to a proximal end. The continuous grooves allow continuous rotation of the end effector 300 and radial expansion and contraction of the wings 302 as one or more pins slide along the grooves. A user can thus select any rotational amount and radial expansion or contraction for application of energy.

Using one of the preceding approaches to allow rotation of the end effector and wings provides a number of advantages. Advantages of a rotating mechanism over a structure which includes more wings are that it reduces the number of required channels and simplifies manufacturing. Because the rotating mechanism requires a smaller number of wings/electrodes than do other designs, a smaller number of wires is needed. As such, the lumen of the catheter can accommodate higher gauge wires and thicker insulation for those wires while maintaining an acceptable lumen diameter and overall catheter diameter (French size). This feature would permit the use of higher voltage electrical pulses that may be required to create adequately deep ablation lesions with the pulsed field technique. This feature also permits the irrigation of electrodes in each wing while maintaining an acceptable lumen diameter and overall catheter diameter (French size). Such a configuration also provides more flexibility to conform to the pulmonary vein anatomy, and enables precise/predictable lesion overlap.

Actuation of mapping/recordation functionality, energy ablation, and/or irrigation can be controlled by external devices, such as various mapping system(s), energy generator(s) to provide various types of ablation energy (such as RF energy or energy adapted for electroporation or pulsed field ablation), computer system(s), irrigation system(s), fluid reservoir(s), etc., that are in electrical and fluid communication with the various wire(s), infusion tube(s), etc. that extend proximally from the handle 100. The handle can additionally include any number of features, such as additional steering mechanisms for steering the end effector and/or deflecting the end effector with respect to the handle and/or the elongate body during placement and orientation, actuation hubs, levers, buttons or the like for controlling the actuator, and for controlling recordation, mapping, fluid delivery, and energy delivery.

While a variety of embodiments of the catheter 10 are provided above, it will be appreciated that some embodiments of the catheter 10 can incorporate various additional functionality and structures known in the art, such as being configured to position and deliver a cardiac valve, configured to cryoablate tissue, and/or configured to laser ablate tissue. For example, embodiments of the catheter 10 can be used during catheter placement of cardiac valves. In such examples, the ability to independently rotate an end effector configured to deliver and place a cardiac valve is especially beneficial.

Additionally, embodiments of the handle are not limited to use only with the end effector 300. Embodiments of the handle 100 with a guided actuation control mechanism and an ability to rotate an end effector, similar to those illustrated in FIGS. 19 and 20, can be incorporated into a variety of different medical devices. A person skilled in the art will also appreciate that various other handle assemblies known in the art can be used in combination with the various elongate body and end effector embodiments disclosed herein. Additionally, in some embodiments, additional sheaths may be used in conjunction with the catheter 10 to aid in placement and stabilization of the catheter, such as may be used when placing and stabilizing positions of catheters used in cardiac electrophysiological procedures.

In use, when being deployed or removed from a patient, the end effector 300 can be in the first configuration to allow for easier and safer passage through narrow openings, such as through various passages, openings, veins, valves, chambers of the heart, etc. As such, the rotatable hub 120 can be in its distal-most position relative to the handle 100 and the actuator 250 can be retracted proximally, as illustrated in FIGS. 23A-23B. During placement, the steering mechanism 106 can be selectively rotated to steer the elongate body 200 and the end effector 300, as desired. Additionally while in the first configuration, the distal electrode 330 can be selectively activated by a user to allow spot recording, mapping, and/or irrigated ablation of tissue by positioning the distal electrode 330 adjacent to the target tissue. The proximal and mid-electrodes 310, 320 can be selectively deactivated to prevent any interference with surrounding tissue or can be selectively activated, as needed.

As the end effector 300 is maneuvered into a passageway or opening to be recorded, mapped, and/or ablated, such as a pulmonary vein, the end effector 300 can be selectively transitioned to the second configuration to radially expand the wings 302 into the passage. As discussed above, the wings 302 can be radially expanded to a variety of different sizes depending on the size of the passage by advancing distally or retracting proximally the actuator 250, which can be guided through use of the actuation control mechanism 110 on the handle 100 as illustrated in FIGS. 24A-24C for a smaller passage and FIGS. 24D-24J for a larger passage. As the wings 302 are expanded radially, the proximal electrodes 310 are positioned adjacent to target tissue encircling the end effector 300, and the user can selectively actuate the proximal electrodes 310 for recording, mapping, and/or ablation. Depending on a size of the passage being treated, the proximal electrodes 310 can be activated one or more times and the end effector 300 can be rotated one or more times as discussed above to ensure accurate recording of any electrical impulses and/or thorough ablation of the target tissue. Even when targeting irregularly shaped anatomy, the wings 302 can position the proximal electrodes 310 adjacent to the target tissue given their flexibility and maneuverability. During treatment the encircling target tissue, the distal and mid-electrodes 320, 330 can be selectively deactivated to prevent any interference or can be selectively activated, as needed.

As one example, the end effector 300 can be used to treat atrial fibrillation by electrically isolating one or more pulmonary veins through tissue ablation. When radially expanded in the second configuration, the proximal electrodes 310 can be used to create a series of overlapping ablation lesions around an inner surface of each pulmonary vein, similar to FIGS. 24C and 24J that each illustrate surrounding target tissue 500, 502 that has been entirely ablated, in order to electrically isolate the pulmonary vein(s) from the atria and thereby block electrical impulses originating in the pulmonary veins from entering the atria. The wings 302 can also allow blood flow through the pulmonary vein even when positioned in the pulmonary opening, which reduces or eliminates blood flow occlusion and prevents increased pressure from any restricted blood flow. After ablation, the proximal electrodes 310 can also be used to establish that electrical conduction has been successfully blocked between the atrium and the pulmonary vein through electrical impulse recording and/or mapping. As such, the amount of required image guided manipulation of the catheter 10 can be reduced or eliminated, and the single catheter 10 can be used rather than multiple mapping and ablation catheters.

The end effector 300 can also be selectively transitioned into the third configuration by advancing the activator 250 distally and retracting the rotatable hub 120 proximally relative to each other to move the mid-electrodes 320 distally into alignment with the distal electrode 330. Additionally, in some embodiments, the outer sheath 270 can be used, as discussed above and illustrated in FIGS. 10C-10G. The distal and mid-electrodes 320, 330 can be used to selectively record, map, and/or ablate a wide surface area, and the planar orientation of the electrodes 320, 330 can assist in stabilizing the electrodes against any target tissue. During recording, mapping, and/or ablation, the proximal electrodes 310 can be selectively deactivated to prevent any interference or can be selectively activated, as needed. In one exemplary procedure, the end effector 300 can be used to detect and map any electrical activity on a wall of an atrium, such as the posterior wall of the left atrium, that can trigger atrial fibrillation. Once mapped, the target tissue can be ablated by creating a series of overlapping lesions on the posterior wall either to eliminate any detected sites of spontaneous electrical activity and/or to electrically isolate the region in which the electrical activity is occurring. As will be appreciated, such a procedure can also be performed when the end effector 300 is in the first configuration.

Furthermore, some embodiments of the catheter can include a lasso-like structure that can assist in positioning or anchoring a catheter within a vein, such as by centering the catheter relative to a central axis of a pulmonary vein of a patient. FIGS. 28A-28D illustrate an embodiment of an end effector 400 on a distal end of an elongate body, similar to end effector 300 and elongate body 200, with a plurality of wings 402, a plurality of electrodes 410, and irrigation and rotation mechanisms. A lasso 420 attaches to and extends distally from the end effector 400 to help stabilize the distal end of the catheter in a center of a vein, such as a pulmonary vein. The lasso 420 has an elongate body 422 and a circular or coiled head 424, and the circular head 424 is expandable to make contact with an inner surface of a vein, such as a pulmonary vein. The circular head 424 can optionally have a plurality of electrodes 426 spaced around the head to come into contact with the inner wall of the pulmonary vein when the head expands. The illustrated electrodes 426 are recording electrodes used to monitor electrical activity in the wall of the pulmonary vein. However, the electrodes 426 can be used for a variety of purposes, such as ablation, mapping, etc. The electrodes 426 are connected to wires that traverse the inner lumen of the catheter so that they can be connected to various devices, such as an external electrical recording device. The lasso 420 can be made from a variety of materials, such as spontaneous or self-expanding shape memory materials.

Figure 28B:
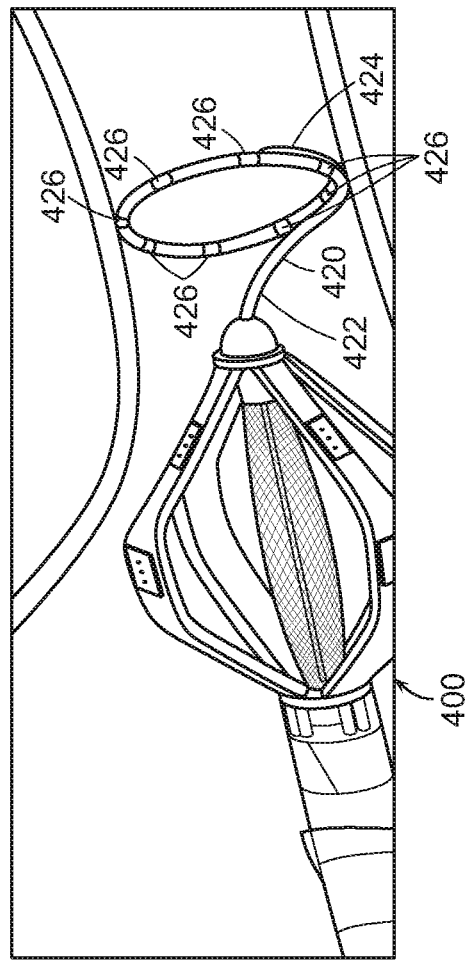
FIG. 28B is a perspective view of the distal end of the catheter of FIG. 28A in a pulmonary vein.
Figure 28A:
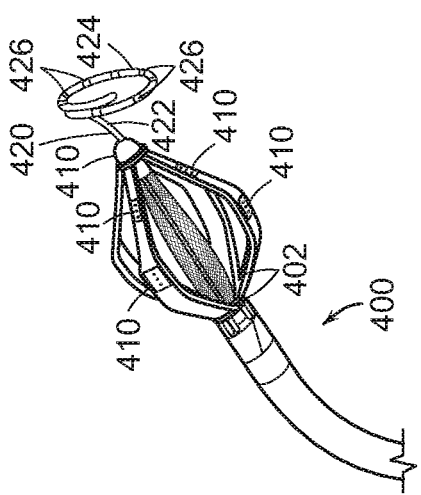
FIG. 28A is a perspective view of another embodiment of a distal end of a catheter.
Figure 28C:
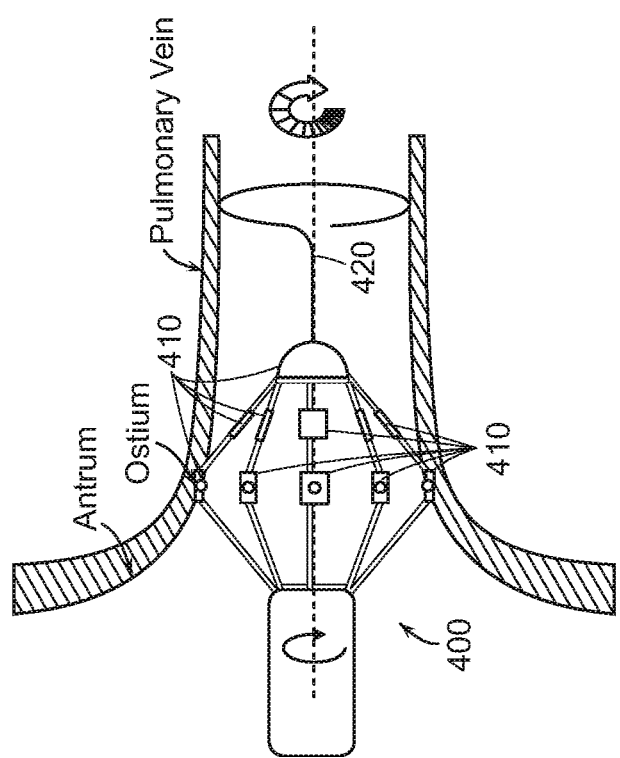
FIG. 28C is a simplified side view of the distal end of the catheter of FIG. 28A in a pulmonary vein.
Figure 28D:
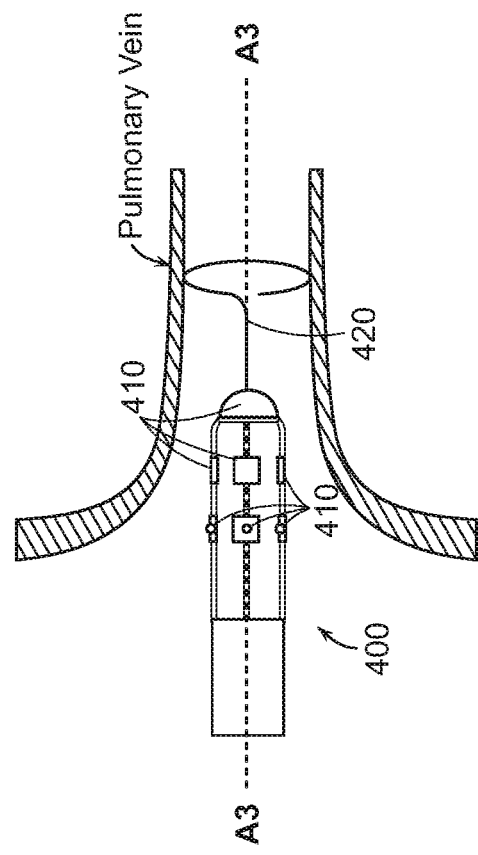
FIG. 28D is a simplified side view of the distal end of the catheter of FIG. 28A in a pulmonary vein expanded to conform to the ostium.
Figure 28E:
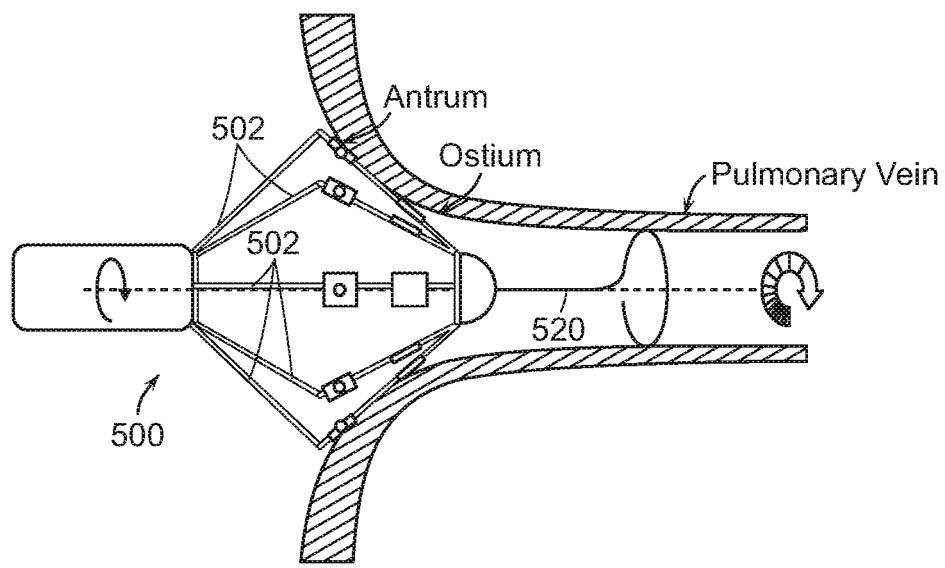
FIG. 28E is a simplified side view of another embodiment of a distal end of a catheter in a pulmonary vein expanded to conform to the antrum.
Figure 28F:
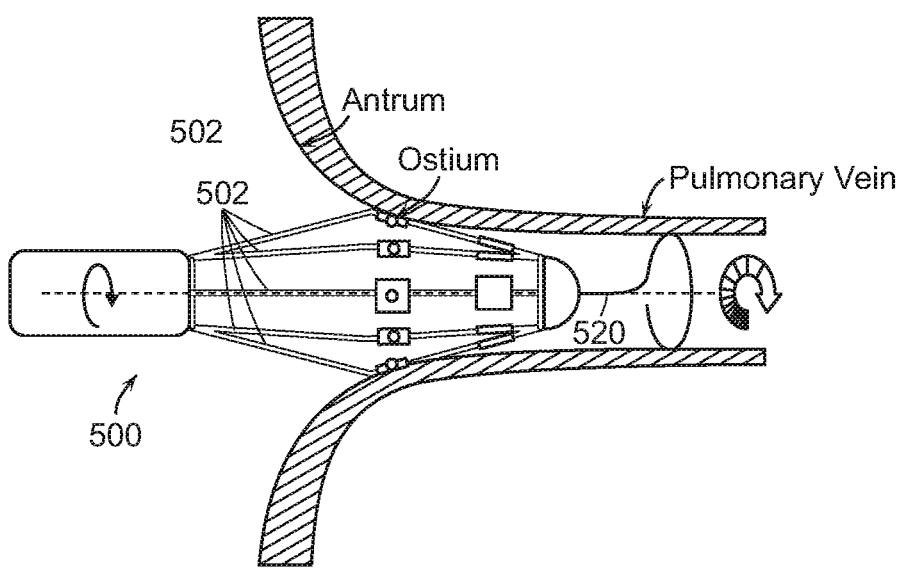
FIG. 28F is a simplified side view of the distal end of the catheter of FIG. 28E in a pulmonary vein expanded to conform to the ostium.

In use, the end effector 400 with the lasso 420 can be introduced into a pulmonary vein by placing a removable sheath over part or all of the end effector 400 to straighten the lasso 420 to a linear configuration, advancing the end effector 400 into the pulmonary vein, and at least partially withdrawing the sheath to free the lasso 420. Once free, at least a distal portion of the lasso 420 spontaneously expands and coils to form the circular head 424 which can come into contact with inner surfaces of the pulmonary vein. For example, FIG. 28C illustrates the end effector 400 in a linear configuration during initial placement while the lasso 420 expands into the circular or coiled configuration to assist in centering and positioning the end effector 400 along a central axis A3 of the pulmonary vein. Once the lasso 420 is fully expanded, as illustrated in FIG. 28D, the end effector 400 can be expanded to bring the electrodes 420 into contact with the pulmonary vein for use, such as through rotation movements to create lesions at the ostium. After use, the sheath can be re-advanced over the end effector 400 and the lasso 420 to re-straighten the lasso 420 to the linear configuration for purposes of withdrawing or moving the end effector. While the end effector 400 illustrated in FIGS. 28A-28D has two bend points on each wing, a lasso can be used with a variety of different end effectors. FIGS. 28E and 28F illustrate another embodiment of an end effector 500 with a lasso 520, similar to end effector 400. The end effector 500 has a plurality of wings 502 with a single bend point, similar to the wings on end effector 300a. FIG. 28E illustrates the end effector expanded to conform to the antrum, and FIG. 28F illustrates the end effector expanded to conform to the ostium.

While specific electrodes are mentioned above for use in each configuration, any of the electrodes can be selectively used for recordation, mapping, and/or ablation in any of the configurations. In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

In the present disclosure, like-numbered components of the embodiments generally have similar features, and thus within a particular embodiment each feature of each like-numbered component is not necessarily fully elaborated upon. Sizes and shapes of the devices described herein, and the components thereof, can depend at least on the anatomy of the subject in which the devices will be used, the size and shape of components with which the devices will be used, and the methods and procedures in which the devices will be used. The figures provided herein are not necessarily to scale. Although the devices and methods disclosed herein are generally directed to surgical techniques, they can also be used in applications outside of the surgical field. Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. An ablation catheter, comprising:
    an elongate body having proximal and distal ends with an inner lumen extending there between; and
    an expandable end effector extending distally beyond the distal end of the elongate body and configured to deliver energy to tissue, the expandable end effector having first, second, and third configurations, wherein in the first configuration, the expandable end effector is substantially linear and extends along a longitudinal axis extending through the elongate body and expandable end effector and is configured to form a single point lesion or a linear lesion, in the second configuration the expandable end effector extends radially outward from the longitudinal axis, and in the third configuration a portion of the expandable end effector faces distally and extends in a plane substantially perpendicular to the longitudinal axis.

2. The ablation catheter of claim 1, wherein a diameter of the expandable end effector in the second configuration is larger than a diameter of the expandable end effector in the first configuration.

3. The ablation catheter of claim 1, wherein a diameter of the expandable end effector in the third configuration is larger than a diameter of the expandable end effector in the first configuration.

4. The ablation catheter of claim 1, wherein the expandable end effector is formed in part or in its entirety from a flexible metal material.

5. The ablation catheter of claim 1, wherein the expandable end effector has a plurality of electrodes disposed thereon.

6. The ablation catheter of claim 5, wherein at least one of the plurality of electrodes can be independently selectively activated or deactivated.

7. The ablation catheter of claim 5, wherein at least one electrode is configured so only the portion of the electrode designed to be in contact with tissue is electrically conductive and the remainder is electrically insulated.

8. The ablation catheter of claim 5, further comprising irrigation tubing configured to supply irrigation fluid to at least one of the plurality of electrodes.

9. The ablation catheter of claim 1, wherein the expandable end effector is configured to form a substantially spherical or polyhedral shape in the second configuration.

10. The ablation catheter of claim 1, wherein the second configuration of the expandable end effector is shaped to create lesions in the antrum or ostium of a pulmonary vein of a patient.

11. The ablation catheter of claim 1, wherein the expandable end effector is configured to deliver at least one of radiofrequency energy, energy configured for electroporation, or pulses of a monophasic or biphasic configuration to tissue.

12. The ablation catheter of claim 1, further comprising an actuator operatively coupled to the expandable end effector such that linear translation of the actuator is configured to move the expandable end effector between the first configuration, the second configuration, and the third configuration.

13. The ablation catheter of claim 1, further comprising a structure extending distally from the end effector and configured to assist in positioning or anchoring the catheter.

14. The ablation catheter of claim 1, wherein the end effector has a plurality of wings.

15. The ablation catheter of claim 1, wherein the elongate body contains a flexible braid configured to block energy from spreading to blood and tissue not in direct contact with or adjacent to an electrode used for delivering ablation energy.

16. The ablation catheter of claim 1, wherein the end effector is configured to rotate relative to the elongate body.

17. The ablation catheter of claim 1, further comprising a lasso structure extending distally from the end effector.

18. An ablation catheter, comprising:
an elongate body having proximal and distal ends with an inner lumen extending there between; and
an expandable end effector extending distally beyond the distal end of the elongate body and configured to deliver energy to tissue, the expandable end effector being moveable between first, second, and third configurations, wherein in the first configuration the expandable end effector is configured to form a single point lesion or linear lesion on tissue, in the second configuration in which the expandable end effector is configured to form a circumferential lesion on tissue, and in the third configuration configured to form substantially co-planar lesions on tissue distal to the expandable end effector.

19. The ablation catheter of claim 18, wherein a diameter of the expandable end effector in the second configuration is larger than a diameter of the expandable end effector in the first configuration.

20. The ablation catheter of claim 18, wherein a diameter of the expandable end effector in the third configuration is larger than a diameter of the expandable end effector in the first configuration.

21. The ablation catheter of claim 18, wherein the expandable end effector is formed in part or in its entirety from a flexible metal material.

22. The ablation catheter of claim 18, wherein the expandable end effector has a plurality of electrodes disposed thereon.

23. The ablation catheter of claim 22, wherein at least one of the plurality of electrodes may be independently selectively activated or deactivated.

24. The ablation catheter of claim 22, wherein at least one electrode is configured so only the portion of the electrode designed to be in contact with tissue is electrically conductive and the remainder is electrically insulated.

25. The ablation catheter of claim 22, further comprising irrigation tubing configured to supply irrigation fluid to at least one of the plurality of electrodes.

26. The ablation catheter of claim 18, wherein the second configuration of the expandable end effector is shaped to create lesions at in the antrum or ostium of a pulmonary vein of a patient.

27. The ablation catheter of claim 18, wherein the expandable end effector is configured to deliver at least one of radiofrequency energy, energy configured for electroporation, or pulses of a monophasic or biphasic configuration to tissue.

28. The ablation catheter of claim 18, wherein the ablation catheter also includes a structure extending distally from the end effector which can assist in positioning or anchoring the catheter.

29. The ablation catheter of claim 18, wherein the end effector has a plurality of wings.

30. The ablation catheter of claim 18, wherein the elongate body contains a flexible braid configured to block energy from spreading to blood and tissue not in direct contact with or adjacent to an electrode used for delivering ablation energy.

* * * * *